US012577584B2

(12) United States Patent
Keck

(10) Patent No.: US 12,577,584 B2
(45) Date of Patent: Mar. 17, 2026

(54) NON-HLA MATCHED HUMANIZED NSG MOUSE MODEL WITH PATIENT-DERIVED XENOGRAFT

(71) Applicant: The Jackson Laboratory, Bar Harbor, ME (US)

(72) Inventor: James Keck, Granite Bay, CA (US)

(73) Assignee: The Jackson Laboratory, Bar Harbor, ME (US)

( * ) Notice: Subject to any disclaimer, the term of this patent is extended or adjusted under 35 U.S.C. 154(b) by 939 days.

(21) Appl. No.: 17/569,660

(22) Filed: Jan. 6, 2022

(65) Prior Publication Data

US 2022/0127638 A1 Apr. 28, 2022

Related U.S. Application Data

(60) Division of application No. 15/850,053, filed on Dec. 21, 2017, now Pat. No. 11,248,236, which is a continuation of application No. PCT/US2016/038622, filed on Jun. 22, 2016.

(60) Provisional application No. 62/183,386, filed on Jun. 23, 2015.

(51) Int. Cl.
| | |
|---|---|
| *C12N 15/85* | (2006.01) |
| *A01K 67/0271* | (2024.01) |
| *A01K 67/0278* | (2024.01) |
| *C07K 14/55* | (2006.01) |
| *C07K 14/705* | (2006.01) |
| *C12N 5/0775* | (2010.01) |
| *G01N 33/50* | (2006.01) |

(52) U.S. Cl.
CPC ...... *C12N 15/8509* (2013.01); *A01K 67/0271* (2013.01); *A01K 67/0278* (2013.01); *C07K 14/55* (2013.01); *C07K 14/70596* (2013.01); *C12N 5/0663* (2013.01); *G01N 33/5088* (2013.01); *A01K 2207/12* (2013.01); *A01K 2207/15* (2013.01); *A01K 2217/075* (2013.01); *A01K 2227/105* (2013.01); *A01K 2267/0331* (2013.01); *A01K 2267/0362* (2013.01); *A01K 2267/0387* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 11,248,236 B2 | 2/2022 | Keck et al. | |
| 2007/0118914 A1* | 5/2007 | Banchereau | A01K 67/0271 800/18 |
| 2013/0042330 A1 | 2/2013 | Murphy et al. | |
| 2014/0101786 A1* | 4/2014 | Sykes | A61K 40/4272 424/277.1 |
| 2015/0283269 A1 | 10/2015 | An et al. | |
| 2022/0127639 A1 | 4/2022 | Keck | |

FOREIGN PATENT DOCUMENTS

| | | |
|---|---|---|
| EP | 2388330 A1 | 11/2011 |
| RU | 2425880 C2 | 8/2011 |
| WO | WO 2005/013682 A2 | 2/2005 |

OTHER PUBLICATIONS

Wege et al., Co-Transplantation of Human Hematopoietic Stem Cells and Human Breast Cancer Cells in NSG Mice. A Novel Approach to Generate Tumor Cell Specific Human Antibodies. mAbs, 2014. 6(4): 968-977.*
Wege et al., Humanized Tumor Mice—A New Model to Study and Manipulate the Immune Response in Advanced Cancer Therapy. International Journal of Cancer, 2011. 129: 2194-2206.*
Ito et al. Defucosylated anti-CCR monoclonal Antibody Exercises Potent ADCC-mediated Antitumor Effect in the Novel Tumor-Bearing Humanized NOD/Shi-scid, IL-2Rγnul Mouse Model. Cancer Immunology and Immunotherapy, 2009. 58:1195-1206.*
Wu et al. Analysis and Characterization of Hematopoietic Progenitor Cells From Fetal Bone Marrow, Adult Bone Marrow, Peripheral Blood, and Cord Blood. Pediatric Research, 1999. 46: 163-169.*
International Search Report and Written Opinion in connection with Application No. PCT/US2016/038622 mailed on Sep. 21, 2016.
International Preliminary Report on Patentability in connection with Application No. PCT/US2016/038662 mailed on Jan. 4, 2018.
[No Author Listed] Onco-Hu™ Models: Humanized NSG™ and NSG™-SGM3 Mice for Immuno-Oncology. Jax Mice, Clinical, and Research Services. http://jackson.jax.org/rs/444-BUH-304/images/LT0074_US_Immuno_Oncology_Whitepaper_WEB.pdf [last accessed Jan. 14, 2020].
Billerbeck et al., Development of human CD4+FoxP3+ regulatory T cells in human stem cell factor-, granulocyte-macrophage colony-stimulating factor-, and interleukin-3-expressing NOD-SCID IL2Rγ(null) humanized mice. Blood. Mar. 17, 2011;117(11):3076-86. doi: 10.1182/blood-2010-08-301507. Epub Jan. 20, 2011.
Chung et al., Co-transplantation of human fetal thymus, bone and CD34(+) cells into young adult immunodeficient NOD/SCID IL2Rγ(null) mice optimizes humanized mice that mount adaptive antibody responses. Clin Immunol. Apr. 2015;157(2):156-65. doi: 10.1016/j.clim.2015.02.005. Epub Feb. 25, 2015.
Giuliano et al., Circulating and disseminated tumor cells from breast cancer patient-derived xenograft-bearing mice as a novel model to study metastasis. Breast Cancer Res. Jan. 9, 2015;17(1):3. doi: 10.1186/s13058-014-0508-5.
Graber et al., Abstract P6-06-02: Molecular characterization of a patient-derived xenograft (PDX) resource for triple negative breast cancer. Cancer Research. May 1, 2015;75(9 Suppl).
Hayakawa et al., Busulfan produces efficient human cell engraftment in NOD/LtSz-Scid IL2Rgamma(null) mice. Stem Cells. Jan. 2009;27(1):175-82. doi: 10.1634/stemcells.2008-0583.

(Continued)

*Primary Examiner* — Christopher M Babic
*Assistant Examiner* — Kimberly A Aron
(74) *Attorney, Agent, or Firm* — Wolf, Greenfield & Sacks, P.C.

(57) ABSTRACT

The invention described herein provides non-HLA matched humanized mouse model (e.g., NSG mouse model) with patient-derived xenograft (PDX), as well as methods of making and using the same.

12 Claims, 28 Drawing Sheets

(56) References Cited

OTHER PUBLICATIONS

Hidalgo et al., A pilot clinical study of treatment guided by personalized tumorgrafts in patients with advanced cancer. Mol Cancer Ther. Aug. 2011;10(8):1311-6. doi: 10.1158/1535-7163. MCT-11-0233. Epub Jun. 14, 2011.

Hidalgo et al., Patient-derived xenograft models: an emerging platform for translational cancer research. Cancer Discov. Sep. 2014;4(9):998-1013. doi: 10.1158/2159-8290.CD-14-0001. Epub Jul. 15, 2014.

Ito et al., Current advances in humanized mouse models. Cell Mol Immunol. May 2012;9(3):208-14. doi: 10.1038/cmi.2012.2. Epub Feb. 13, 2012.

Krepler et al., Abstract 2842: Personalized Preclinical Trials in BRAF Inhibitor-Resistant Patient-Derived Xenograft Models of Melanoma Identify c-Met as an effective second line combination therapy target. Cancer Res. Aug. 1, 2015;75(15 Suppl).

Lu et al., Research and application progress of humanized mouse model. Medical Recapitulate. Sep. 2014. 30;20(18):3281-4.

Rick Huntress: "Applying humanized mouse models to immune therapy research". The Jackson Laboratory, Retrieved from the Internet: URL:hllp://tumor-models.com/wp-content/uploads/sites/67 /2016/03/101 0-Rick-Huntress-YESI. Pdf [retrieved on Aug. 25, 2016].

Rick Huntress: "Patient-derived Tumor Xenografls in Humanized NSG Mice: A Model to study immune responses in cancer therapy", Retrieved from the Internet: <URL:http://immune-checkpoinl.com/wp-contenl/uploads/sites/24/2015/01/Day-1-15.45-Rick-Huntress. pdf> [retrieved on Aug. 25, 2016].

Rick Huntress: "Patient-derived Tumor Xenografls in Humanized NSG-SGM3 Mice: A new Immune-oncology platform". The Jackson Laboratory, Retrieved from the Internet: URL http://immune-checkpoint.com/wp-content/uploads/sites/24/2015/11/Day-1-1630-Rick-Huntress.pdf [retrieved on Aug. 25, 2016].

Shultz et al., Human Cancer Growth and Therapy in NOD/SCID/IL2Rγnull (NSG) Mice. Cold Spring Harb Protoc. Jul. 1, 2014;2014(7):694-708. doi: 10.1101/pdb.top073585.

Sun et al., Current situation and application of mouse model with humanized immune system. Laboratory Animal Science. Dec. 2012. 31;29(6):52-4.

Vatakis et al., Antitumor activity from antigen-specific CD8 T cells generated in vivo from genetically engineered human hematopoietic stem cells. Proc Natl Acad Sci U S A. Dec. 20, 2011;108(51):E1408-16. doi: 10.1073/pnas.1115050108. Epub Nov. 28, 2011.

Wang et al., Abstract LB-050: Patient-derived tumor xenografts in humanized NSG mice: a model to study immune responses in cancer therapy, Proceeding: AACR 106th Annual Meeting 2015; Apr. 18-22, 2015; Philadelphia, PA.

Whittle et al., Patient-derived xenograft models of breast cancer and their predictive power. Breast Cancer Res. Feb. 10, 2015;17(1):17. doi: 10.1186/s13058-015-0523-1.

Yao et al., Abstract LB-C01: Patient-derived tumor xenografts in humanized NSG-SGM3 mice: A new immune-oncology platform, AACR; Mol Cancer Ther 2015; 14 (12 Suppl 2) Abstract nr LB-C01.

Yao et al., Abstract LB-C01: Patient-derived tumor xenografts in humanized NSG-SGM3 mice: A new immune-oncology platform. J Clin Oncol 34, 2016 (suppl; abstr 3074).

U.S. Appl. No. 17/569,788, filed Jan. 6, 2022, Pending.

PCT/US2016/038622, Sep. 21, 2016, International Search Report and Written Opinion.

PCT/US2016/038662, Jan. 4, 2018, International Preliminary Report on Patentability.

Choi et al., Lessons from patient-derived xenografts for better in vitro modeling of human cancer. Adv Drug Deliv Rev. Dec. 15, 2014;79-80:222-37. doi: 10.1016/j.addr.2014.09.009. Epub Oct. 13, 2014.

Daniel et al., A primary xenograft model of small-cell lung cancer reveals irreversible changes in gene expression imposed by culture in vitro. Cancer Res. Apr. 15, 2009;69(8):3364-73. doi: 10.1158/0008-5472.CAN-08-4210. Epub Apr. 7, 2009.

Pu et al., Patient-derived tumor immune microenvironments in patient-derived xenografts of lung cancer. J Transl Med. Nov. 26, 2018;16(1):328. doi: 10.1186/s12967-018-1704-3.

Rajesh et al., Th1 and Th17 immunocompetence in humanized NOD/SCID/IL2rγ$^{null}$ mice. Hum Immunol. Jun. 2010;71(6):551-9. doi: 10.1016/j.humimm.2010.02.019. Epub Mar. 26, 2010.

Siolas et al., Patient-derived tumor xenografts: transforming clinical samples into mouse models. Cancer Res. Sep. 1, 2013;73(17):5315-9. doi: 10.1158/0008-5472.CAN-13-1069. Epub Jun. 3, 2013.

Wunderlich et al., AML xenograft efficiency is significantly improved in NOD/SCID-IL2RG mice constitutively expressing human SCF, GM-CSF and IL-3. Leukemia. Oct. 2010;24(10):1785-8. doi: 10.1038/leu.2010.158. Epub Aug. 5, 2010.

Seitz et al., Establishment of a rhabdomyosarcoma xenograft model in human-adapted mice. Oncol Rep. Oct. 2010;24(4):1067-72. doi: 10.3892/or.2010.1067.

Wulf-Goldenberg et al., Intrahepatically transplanted human cord blood cells reduce SW480 tumor growth in the presence of bispecific EpCAM/CD3 antibody. Cytotherapy. Jan. 2011;13(1):108-13. doi: 10.3109/14653249.2010.515577. Epub Sep. 15, 2010. Abstract Only.

* cited by examiner

FIG. 3 hCD45+ Cells (%) in Peripheral Blood at 50 Days post SKOV3 Cancer Cells Inocaulation BR0744 Tumor Growth Curve in NSG Mice vs. Hu-NSG mice

FIG. 4C

SA0209 Tumor Growth Curve in NSG Mice vs. Hu-NSG mice

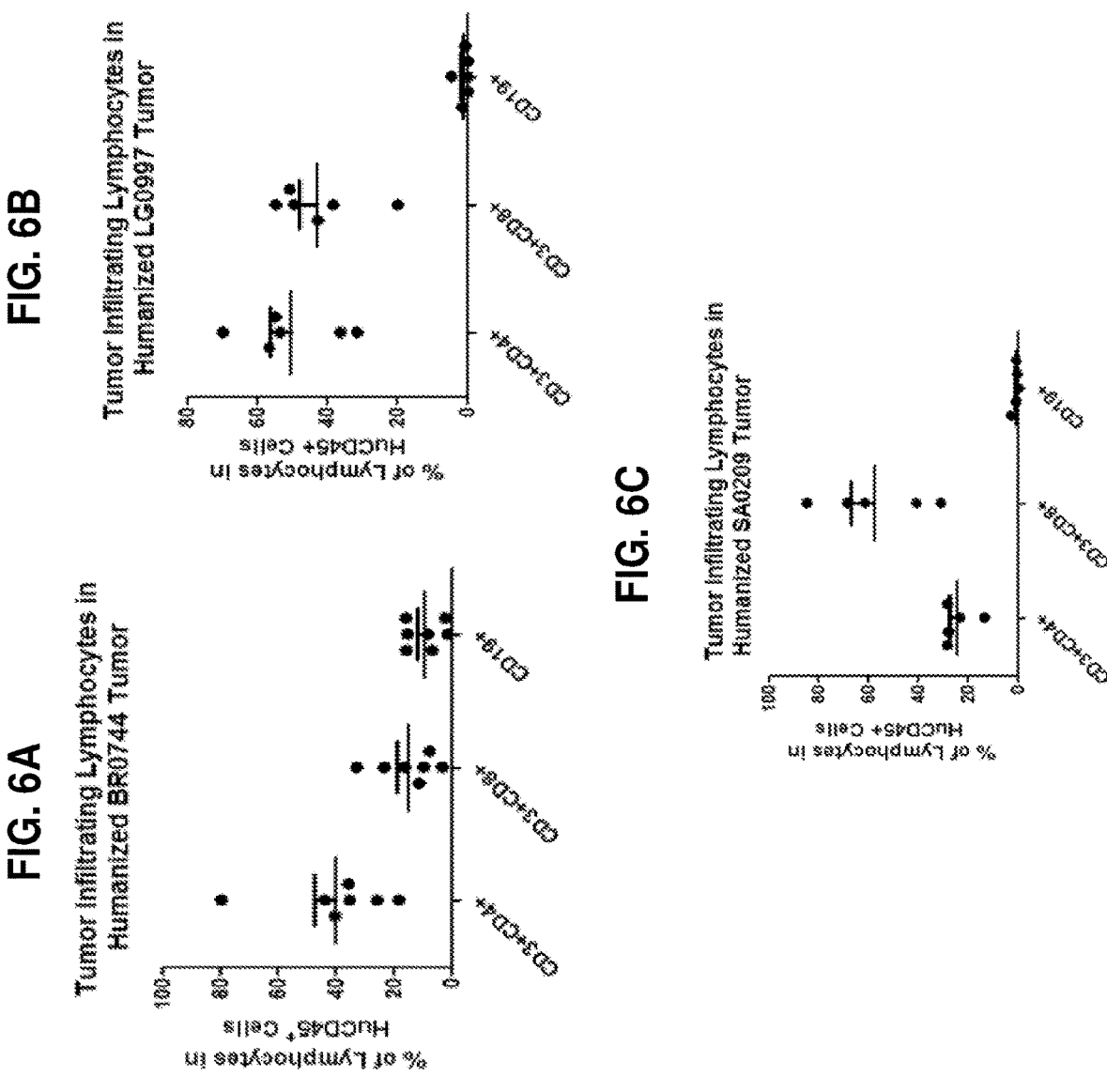

Mean Tumor Volume in CN1572P5 PDX in Hu-NSG Mice on Study Day 21

\* P<0.05: Compared to Vehicle group.
One-way ANOVA followed Dunnett's Multiple Comparsion test.

Mean Tumor Volume in MDA-MD-231 Model in Hu-NSG Mice on Study Day 20

P=0.0059: Compared to Vehicle group. Two-tailed unpaired t test

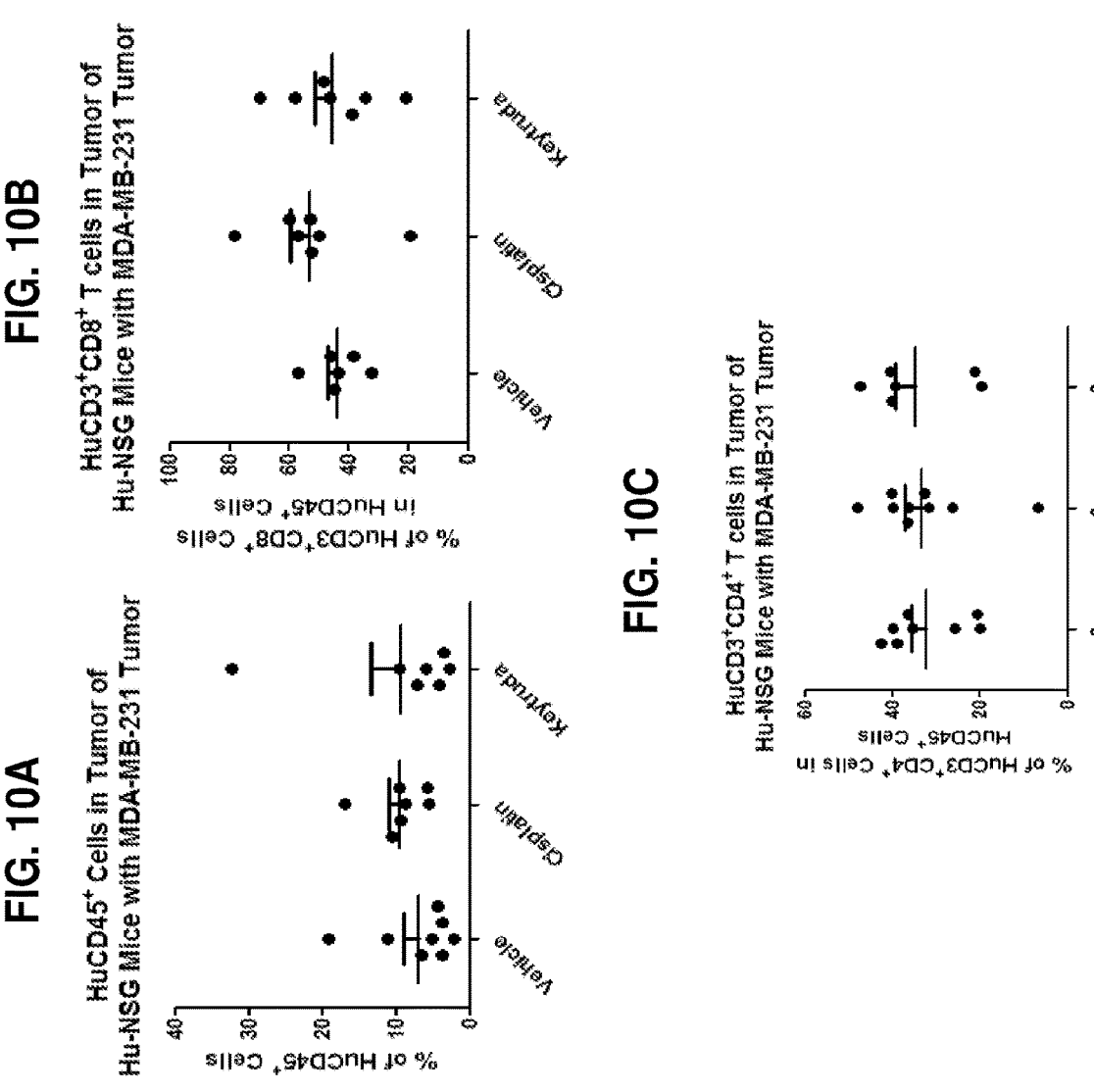

Mean Tumor Volume in BR1126 PDX in Hu-NSG Mice on Study Day 17
***P<0.05: Compared to Vehicle group.
One-way ANOVA followedDunnett's Multiple Comparison test Mean Tumor Volume of TM00098 (BR1126P5) PDX in Hu-NSG Mice

* P=0.0127; Compared to Vehicle group. Two-tailed unpaired t test.

● Vehicle (Saline) ip Q5Dx4
▨ Pembrolizumab (10->5mg/kg) ip Q5Dx4*

Mean Tumor Volume (mm³) +/- SEM

Days
(Day 0 = treatment initiation)

| HLA match | CD34⁺HPC donor | | |
|---|---|---|---|
| | 1 | 2 | 3 |
| Tumor | | | |
| BR1126 | HLA-C, DPA1 | HLA-A,DQA1, DPB1, DPA1 | HLA-C, DPA1 |

- Fresh tumor tissue engraftment
- HuCD45+ in Hu-NSG mice: >25%
- BR1126 PD-L1 surface expression: 56.9%

Mean Tumor Volume in LG1306 PDX in Hu-NSG Mice on Study Day 24

**P<0.05: Compared to Vehicle group.
One-way ANOVA followed Dunnett's Multiple Comparison test Mean Tumor Volume of TM00302 (LG1306P5) PDX
in Hu-NSG Mice

*P<0.05, Vehicle vs Pembrolizumab. Two-tailed unpaired t test

Vehicle (saline) ip Q5Dx6

Pembrolizumab (5mg/kg) ip Q5Dx6*

(Day 0 = treatment initiation)

| HLA match | | CD34+HPC donor | |
|---|---|---|---|
| | | 1 | 2 |
| Tumor | | | |
| LG1306 | | HLA-DRB4, DQA1, DQB1 | No match |

- Fresh tumor tissue engraftment
- HuCD45+ more than 20%
- LG1306 PD-L1 surface expression: 89.1%

FIG. 15F

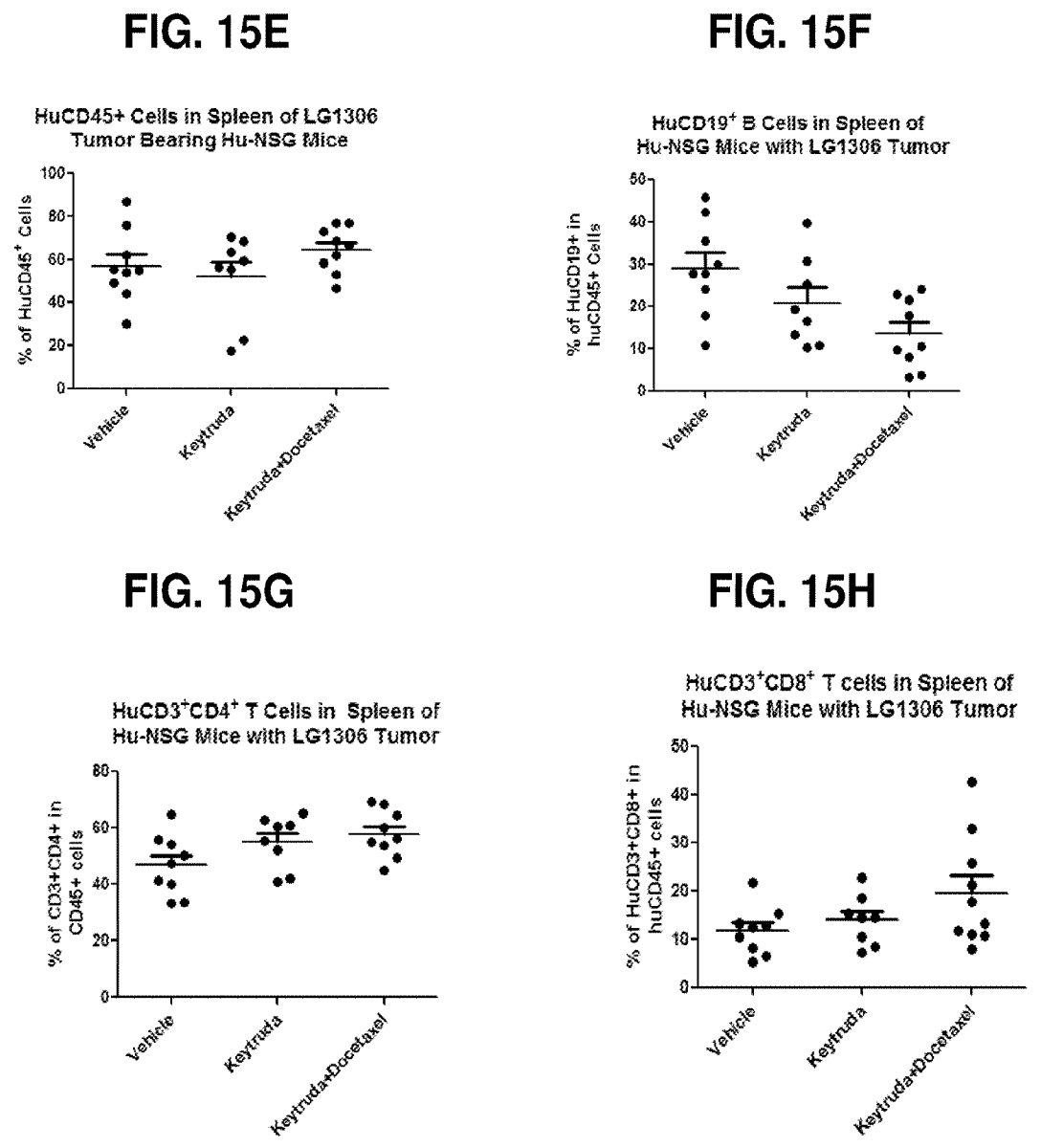

HuCD19⁺ B Cells in Spleen of Hu-NSG Mice with LG1306 Tumor

FIG. 15H

HuCD3⁺CD8⁺ T cells in Spleen of Hu-NSG Mice with LG1306 Tumor

FIG. 15E

HuCD45+ Cells in Spleen of LG1306 Tumor Bearing Hu-NSG Mice

FIG. 15G

HuCD3⁺CD4⁺ T Cells in Spleen of Hu-NSG Mice with LG1306 Tumor

NON-HLA MATCHED HUMANIZED NSG MOUSE MODEL WITH PATIENT-DERIVED XENOGRAFT

REFERENCE TO RELATED APPLICATIONS

The application is a division of U.S. application Ser. No. 15/850,053, filed on Dec. 21, 2017, which is a continuation of International Patent Application No. PCT/US2016/038622, filed on Jun. 22, 2016, which claims the benefit of the filing date under 35 U.S.C. § 119 (e) to U.S. Provisional Patent Application No. 62/183,386, filed on Jun. 23, 2015, the entire contents of each of which are incorporated herein by reference.

BACKGROUND OF THE INVENTION

The immune system of vertebrates is extremely complex and disorders of the immune system are likewise complicated. The vertebrate immune system comprises the innate immune system and the adaptive immune system. The innate immune system, also called the non-specific immune system, includes cells that defend an organism in a non-specific manner. The innate immune system is distinct from the adaptive immune system which specifically recognizes antigens and provides long-term protection. The innate immune system is characterized by antigen-independent response, and exposure of the innate immune system does not result in immunologic memory. Cells of the innate immune system include dendritic cells, mast cells, macrophages, natural killer cells, neutrophils, basophils and eosinophils.

Due to the complexity of the vertebrate immune system, diseases and defects are often difficult to characterize and treat. There is a continuing need for animal models which allow for isolation of aspects of the immune response, providing methods and compositions useful, for example, for identification of effective medical and pharmaceutical treatments of diseases and defects of the immune system.

Immunodeficient mice are frequently used as models of growth and differentiation of normal and abnormal xenogeneic cells. Immunodeficient mice are characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger, M. A et al., *Science*, 248:1517-1523, 1990; and Schatz, D. G. et al., *Cell*, 59:1035-1048, 1989) Immunodeficient mice may have any of these or other defects which result in abnormal immune function in the mice.

Particularly useful immunodeficient mouse strains are NOD.Cg-Prkdc$^{scid}$ Il2rg$^{tm1Wjl}$/SzJ, commonly referred to as NOD scid gamma (NSG) mice, described in detail in Shultz et al., *J. Immunol.*, 174:6477-6489, 2005; and NOD.Cg-Rag1tm1Mom Il2rg$^{tm1Wjl}$/SzJ, Shultz et al., *Clin. Exp. Immunol.*, 154(2):270-284, 2008, commonly referred to as NRG mice.

In some experiments, such immunodeficient mouse strains are humanized by engrafting parts of the human immune system into the immunodeficient mouse. Such humanized mouse models are particularly powerful research tools. While most experimental studies are done in rodents, such as mouse, the outcomes predicted by murine studies are not always representative of actual outcomes in humans. Creating humanized mouse model permits study of human-specific infections and therapies in mice, thus enabling clinically relevant in vivo studies of human cells, tissues, and immune systems, without the drawback of putting patients at risk.

While various immunodeficient mouse strains are available, each has drawbacks and limitations in use. In particular, efficient engraftment of xenogeneic stem cells, such as xenogeneic hematopoietic stem cells (HSC), in immunodeficient mice requires irradiation of the recipient mouse or conditioning by radiomimetic drugs such as busulfan. Irradiation of newborn mice results in small, frail mice, and some of the irradiated mice die prematurely. Further, there is concern about the effect of irradiation on hematopoietic development of the treated animals. See, for example, Nielsen et al., *Blood*, 110(3):1076-1077, 2007.

Thus, there is a continuing need for methods and compositions for engraftment of xenogeneic hematopoietic stem cells in immunodeficient mouse strains and using the same.

SUMMARY OF THE INVENTION

One aspect of the invention provides a humanized immunodeficient non-obese diabetic (NOD) mouse, wherein the mouse: (1) is homozygous for the scid mutation; (2) has an IL-2 receptor gamma chain deficiency; (3) is engrafted with CD34$^+$ human hematopoietic stem cells (HSCs); (4) is inoculated with a human patient-derived xenograft (PDX); wherein the HSCs and the PDX are non-HLA matched (e.g., only partially matched or not matched).

In certain embodiments, the scid mutation is Cg-Prkdc$^{scid}$.

In certain embodiments, the IL-2 receptor gamma chain deficiency is a genetic null mutation, such as Il2rg$^{tm1Wjl}$. In other embodiments, the IL-2 receptor gamma chain deficiency is a truncation mutation in the IL-2R gamma chain (e.g., latching the extracellular or intracellular domain).

In certain embodiments, the mouse is NOD.Cg-Prkdc$^{scid}$ Il2rg$^{tm1Wjl}$/SzJ (i.e., NOD scid gamma (NSG)).

In certain embodiments, the mouse is a female NSG mice further surgically implanted with human thymus and liver fragments, e.g., the hu-BLT NSG™ mouse (BLT mouse of BLT humanized mouse).

In certain embodiments, the mouse is engrafted with human peripheral blood mononuclear cells, e.g., the hu-PBMC NSG™ mouse (or PBMC humanized mouse).

In certain embodiments, the mouse further comprises transgenes constitutively expressing human interleukin-3 (IL-3), human granulocyte/macrophage-stimulating factor (GM-CSF), and/or human Steel factor (SF).

In certain embodiments, the CD34$^+$ human HSCs are engrafted through tail vein injection (preferably the mouse is female), facial vein injection, intracardiac injection, or intrahepatic injection.

In certain embodiments, the CD34$^+$ human HSCs are engrafted to the mouse at the age of about 2-4 weeks, e.g., about 2 weeks, 3 weeks, or 4 weeks.

In certain embodiments, the CD34$^+$ human HSCs are engrafted to the mouse at the age of about 24-72 hrs, e.g., about 24 hrs, 36 hrs, 48 hrs, 60 hrs, 72 hrs, or 90 hrs.

In certain embodiments, the CD34ig.$^+$ human HSCs are engrafted after whole body irradiation of the mouse (e.g., at a dose of about 1, 2, 3, 4, 5, 10, 20, 100, 200, 300, 400, 500, 600, 700, 800, 900, 1000, 1100, 1200, or 1300 cGy, or between any of the two recited doses herein, such as 100-300 cGy or 700-1300 cGy, etc.).

In certain embodiments, the human PDX is inoculated to the mouse about 2 weeks after the mouse is engrafted with the CD34$^+$ human HSCs. In certain embodiments, the human PDX is inoculated to the mouse about 12 weeks after the mouse is engrafted with the CD34+ human HSCs. In certain embodiments, the human PDX is inoculated to the mouse about 1, 2, 3, 4, 5, 6, 7, 8, 9, 10, 11, 12, 13, 14, or 15 weeks (or a range defined by any of the two numeric values) after the mouse is engrafted with the CD34+ human HSCs.

In certain embodiments, the human PDX is from a primary patient sample. In certain embodiments, the human PDX is from an archived tumor sample that has been passaged as a xenograft for at least one generation. In certain embodiments, the human PDX has a low passage number, e.g., one that has been passaged as a xenograft or in culture for no more than 5, 4, 3, 2, or 1 generations. In certain embodiments, the human PDX retains genetic and/or phenotypic heterogeneity of the human cancer from which it is derived. In certain embodiments, the human PDX is from a treatment-naïve patient. In certain embodiments, the human PDX is from a treatment-resistant patient.

In certain embodiments, the human PDX is any one or more of the PDX from the PDX LIVE™ tumor maintained and available from the Jackson Laboratory. The Jackson Laboratory provides access to a wider range of patient-derived xenograft (PDX) cancer models at earlier passage numbers, as a collection of PDX LIVE™ tumor engrafted NSG mice. This collection of readily available, off-the-shelf, PDX tumors can be maintained in the NSG mouse background, and any of the PDX can also be in the subject non-HLA matched humanized immune-deficient mouse (e.g., NSG, NSGS, BLT, etc.).

For example, in certain embodiments, the PDX tumor is a breast tumor, including invasive ductal carcinoma. Representative breast tumor includes TM00089, TM00095-TM00099, TM00103 and TM 00129 (The TM numbers represent the PDX Model ID in the Mouse Tumor Biology Database at tumor dot informatics dot jax dot org slash mtbwi slash index dot do). In certain embodiments, the PDX tumor is a lung cancer, such as one with mutations in ALK, KRAS, TP53, EGFR, or combination thereof. See TM00046, TM00186, TM00192-TM00194, TM00200, TM00202-TM00204, TM00206, TM00208, TM00213, TM00214, TM00219, TM00222, TM00226, TM00233, TM00253, TM00302, TM00355, TM00784, TM00832. In certain embodiments, the PDX tumor is a bladder cancer (e.g., TM00015). In certain embodiments, the PDX tumor is a brain cancer (e.g., TM00058 and TM01087). In certain embodiments, the PDX tumor is a colon cancer (e.g., TM00164 and TM00165). In certain embodiments, the PDX tumor is an ovarian cancer (e.g., TM00334, TM00335, TM00391).

In certain embodiments, the human PDX is a xenograft from an ovarian cancer, a lung cancer such as a non-small cell lung cancer (NSCLC), a bladder cancer, a lymphoma (such as AML, CML, ALL, CLL, DLBCL (diffuse large B-cell lymphoma)), a breast cancer such as a triple-negative breast cancer (TNBC), a brain cancer, a pancreatic cancer, a prostate cancer, a colon cancer, a colorectal cancer, an endometrial cancer, a gastric/GIST cancer, a heptocellular cancer, a kidney/renal cancer, a skin cancer (such as melanoma), a soft tissue carcinoma, a sarcoma, or a cancer cell line.

In certain embodiments, the human PDX is a xenograft from a tumor/cancer that expresses PD-L1 and/or PD-L2.

In certain embodiments, about $0.5\text{-}10\times10^6$ cells (e.g., about $1\text{-}9\times10^6$ cells, about $2\text{-}8\times10^6$ cells, about $3\text{-}7\times10^6$ cells, about $4\text{-}6\times10^6$ cells, or about $5\times10^6$ cells) of the human PDX are inoculated.

In certain embodiments, percentage of human CD45+ cells in peripheral blood of the mouse reaches about 20-30% at about 50 days post PDX inoculation (or at about 9 weeks post HSCs engraftment).

In certain embodiments, the mouse is administered an anti-cancer compound. For example, the anti-cancer compound may be 5-FU, Avastin, cisplatin, carboplatin, keytruda, docetaxel, or combination thereof. In certain embodiments, the anti-cancer compound is a chemotherapeutic reagent. In certain embodiments, the anti-cancer compound is a preclinical drug. In certain embodiments, the anti-cancer compound is an immuno-modulator, such as a modulator of PD-1 or ligand/receptor thereof, or a modulator of CTLA-4 or ligand/receptor thereof. In certain embodiments, the anti-cancer compound is an anti-PD-1 and/or anti-PD-L1 agent, such as an anti-PD-1 antibody and/or an anti-PD-L1 antibody.

The anti-PD-1 antibody blocks interactions between PD-1 and its ligands, PD-L1 and PD-L2, while the anti-PD-L1 antibody blocks interactions between PD-L1 and both PD-1 and B7-1 (CD80), which is implicated in the down-modulation of T-cell responses.

Several PD-1 and PD-L1 inhibitors are in clinical development in early- and late-stage clinical trials across a wide variety of cancers. Any one or more of the PD-1 and PD-L1 inhibitors can be used as anti-cancer agent of the invention.

Representative anti-PD-L1 agents include the following agents in Table 1, and representative anti-PD-1 agents include the following in Table 2, both adapted from Dolan and Gupta, *Cancer Control*, 21(3):231-7, 2014 (incorporated by reference).

For example, BMS-936559/MDX-1105 is a fully human, high affinity, immunoglobulin (Ig) G4 monoclonal antibody to PD-L1. MPDL3280A is an engineered human monoclonal antibody targeting PD-L1. CT-011/pidilizumab is a humanized IgG1 monoclonal antibody that binds to PD-1. BMS-936558/MDX-1106/nivolumab is a fully human IgG4 monoclonal antibody against PD-1. Pembrolizumab is a highly selective, humanized IgG4-kappa monoclonal antibody with activity against PD-1.

TABLE 1

| Selected Ongoing Clinical Trials of Anti-PD-L1 Drugs | | | |
|---|---|---|---|
| Indication | Compound | Clinical Trials No. | Phase |
| Advanced | BMS-936559 | NCT00729664 | 1 |
| solid tumors | MED14736 | NCT01693562 | 1 |
| Melanoma | MPDL3280A + vemurafenib | NCT01656642 | 1b |
| | MPDI4736 + dabrafenib + trametinib or trametinib alone | NCT02027961 | 1/2 |
| NSCLC | MPDL3280A+ erlotinib | NCT02013209 | 1b |
| | MPDL3280A | NCT01846416 | 2 |
| | MPDL3280A | NCT02031458 | 2 |
| | MPDL3280A vs. docetaxel | NCT01903993 | 2 |
| | MPDL3280A vs. docetaxel | NCT02008227 | 3 |
| | MPDI4736 + tremelimumab | NCT02000947 | 1b |
| RCC | MPDL3280A ± bevacizumab vs. sunitinib | NCT01984242 | 2 |

TABLE 1-continued

| | | Clinical Trials | |
|---|---|---|---|
| Indication | Compound | No. | Phase |
| Solid or hematological malignancies | MPDL3280A | NCT01375842 | 1 |
| Solid tumors | MPDL3280A + bevacizumab and/or chemotherapy | NCT01633970 | 1 |
| | MPDL3280A + cobimetinib | NCT01988896 | 1 |
| | MEDI4736 | NCT01938612 | 1 |
| | MEDI4736 + tremelimumab | NCT01975831 | 1 |
| | MSB0010718C | NCT01943461 | 1 |
| | MSB0010718C | NCT01772004 | 1 |

Selected Ongoing Clinical Trials of Anti-PD-L1 Drugs

PD-L1 = programmed death ligand 1. NSCLC = non-small-cell lung cancer, RCC = renal cell carcinoma.

TABLE 2

Selected Ongoing Clinical Trials of Anti-PD-1 Drugs for Solid Tumors

| | | Clinical | |
|---|---|---|---|
| Indication | Compound | Trials No. | Phase |
| Advanced cancer | AMP-224 | NCT01352884 | 1 |
| Advanced solid tumors | Nivolumab + iliolumbar (anti-KIR) | NCT01714739 | 1 |
| Castration-resistant prostate cancer, melanoma, NSCLC, RCC | Nivolumab | NCT00730639 | 1b |
| Colon | Pembrolizumab | NCT01876511 | 2 |
| Gastric, head and neck, TNBC, urothelial | Pembrolizumab | NCT01848834 | 1 |
| Gastric, pancreatic, small-cell lung cancer, TNBC | Nivolumab ± ipilimumab | NCT01928394 | 1/2 |
| Glioblastoma | Nivolumab ± ipilimumab vs bevacizumab | NCT02017717 | 2 |
| Hepatocellular | Nivolumab | NCT01658878 | 1 |
| Hodgkin lymphoma, myeloma, myelodysplastic syndrome, non-Hodgkin lymphoma | Pembrolizumab | NCT01953692 | 1 |
| Malignant gliomas | Pidilizumab | NCT01952769 | 1/2 |
| Melanoma | Nivolumab ± ipilimumab vs ipilimumab | NCT01844505 | 3 |
| | Nivolumab + ipilimumab vs ipilimumab | NCT01927419 | 2 |
| | Nivolumab + ipilimumab | NCT01024231 | 1 |
| | Nivolumab sequentially with ipilimumab | NCT01783938 | 2 |
| | Nivolumab vs DTIC or carboplatin/paclitaxel after ipilumumab | NCT01721746 | 3 |
| | Nivolumab vs DTIC | NCT01721772 | 3 |
| | Nivolumab + multiple class 1 peptides and montanide ISA 51 VG | NCT01176461 | 1 |
| | Nivolumab + multiple class 1 peptides and montanide ISA 51 VG | NCT01176474 | 1 |
| | Nivolumab | NCT01621490 | 1 |
| | Pembrolizumab vs chemotherapy | NCT01704287 | 2 |
| | Pembrolizumab vs ipilimumab | NCT01866319 | 3 |

TABLE 2-continued

Selected Ongoing Clinical Trials of Anti-PD-1 Drugs for Solid Tumors

| | | Clinical | |
|---|---|---|---|
| Indication | Compound | Trials No. | Phase |
| Melanoma, NSCLC | Pembrolizumab | NCT01295827 | 1 |
| NSCLC | Nivolumab ± gemcitabinecisplatin, pemetrexed/cisplatin, carboplatin/paclitaxel, bevacizumab, erlotinib, ipilimumab | NCT01454102 | 1 |
| | Nivolumab vs docetaxel | NCT01673867 | 3 |
| | Nivolumab vs docetaxel | NCT01642004 | 3 |
| | Nivolumab | NCT01721759 | 3 |
| | Nivolumab | NCT01928576 | 2 |
| | Pembrolizumab vs docetaxel | NCT01905657 | 2/3 |
| | Pembrolizumab | NCT02007070 | 1 |
| Pancreatic | Pidilizumab + gemcitabine | NCT01313416 | 2 |
| Prostate | Pidilizumab + sipuleucel-T + cyclophosphamide | NCT01420965 | 2 |
| RCC | Nivolumab + sunitinib, pazopanib, or ipilimumab | NCT01472081 | 1 |
| | Nivolumab | NCT01354431 | 2 |
| | Nivolumab vs everolimus | NCT01668784 | 2 |
| | Nivolumab | NCT01358721 | 1 |
| | Pembrolizumab + pazopanib | NCT02014636 | 1 |
| | Pidilizumab ± dendritic cell/RCC fusion cell vaccine | NCT01441765 | 2 |
| Solid Tumors | Anti-LAG3 (BMS-986016) ± nivolumab | NCT01968109 | 1 |
| | Nivolumab | NCT00836888 | 1 |
| | Nivolumab ± interleukin-21 | NCT01629758 | 1 |
| | AMP-554 | NCT02013804 | 1 |
| Solid tumors, NSCLC | Pembrolizumab | NCT01840579 | 1 |

PD-L1 = programmed death 1, NSCLC = non-small-cell lung cancer, RCC = renal cell carcinoma, TNBC = triple negative breast cancer.

In certain embodiments, the anti-cancer agent is a CTLA-4 antagonist, such as an anti-CTLA-4 antibody (e.g., ipilimumab—FDA-approved CTLA-4 inhibitor for treating melanoma; and Tremelimumab, formerly ticilimumab or CP-675,206, a fully human IgG2 monoclonal antibody produced by Pfizer, and is undergoing human clinical trials for the treatment of cancer).

In certain embodiments, the anti-cancer agent is a combination of a CTLA-4 antagonist and a PD-1 antagonist/PD-L1 antagonist. Since CTLA-4 and PD-1 regulate distinct immune inhibitory pathways, concurrent inhibition of both immune inhibitory pathways may be more efficacious than inhibiting either one alone.

CTLA-4 is a key inhibitory cell surface protein on T cells, and cancer growth may be associated with an imbalance in the natural feedback mechanisms that modulate the immune response. For example, tumors may down-regulate co-stimulatory pathways for T-cell activation, including CD28, CD40, OX40, and CD137. Meanwhile or alternatively, tumors may up-regulate inhibitory immune checkpoint pathways, including LAG-3, CTLA-4, and B7-H3. Preclinical and/or clinical evidence suggests that advanced cancers have been associated with decreased T-cell expression of OX40; tumor evasion of normal immune attack by exploitation of the CTLA-4 immune checkpoint pathway; T-cell expression of CTLA-4 inhibits the anti-tumor response by restricting T-cell activation and proliferation; increased T-cell expression of the immune checkpoint LAG-3 (thus increasing the inhibitory effect on T-cell activation and function); and tumor cell expression of B7-H3, which may impair T-cell-mediated immune responses. Thus the subject mouse may be used to determine whether up-regulating CD28, CD40, OX40, and/or CD137 co-stimulatory pathways, or down-regulating LAG-3, CTLA-4, and/or B7-H3 inhibitory immune checkpoint pathways, can treat any of the PDX tumors.

Tumors also use mechanisms in addition to those mediated by CTLA-4 and PD-1 to evade immune responses. For example, multiple myeloid growth factors are released within the microenvironment of many tumors to signal immature myeloid cells with unique immunosuppressive capacities to expand, including the myeloid cell subpopulations called tumor-associated macrophages (TAMs). TAMs are an abundant population of leukocytes in solid tumors that, in many settings, facilitate, rather than limit tumor progression by, for example, suppressing TIL activity and increasing tumor angiogenesis.

Regulatory T cells ($T_{reg}$) and T helper 2 cells ($T_{H2}$) promoted by TAMs generate strong immunosuppressive actions in the tumor. These cells are normally associated with maintenance of immune tolerance.

Other myeloid cells found in tumors include myeloid-derived suppressor cells (MDSCs), which represent an heterogeneous group of immature cells that include precursors of macrophages, granulocytes, and dendritic cells, defined by their ability to suppress T cell proliferation and to promote angiogenesis. MDSCs use a spectrum of immunosuppressive mechanisms to help tumors evade immunity, most of their effects are directed at suppressing T cells.

Other immune cell populations important in tumor immunity include dendritic cells (DCs) and natural killer (NK) cells. DCs are "professional antigen presenting cells" and are capable of processing unique tumor-specific antigens to activate T and B cells. DCs, therefore, are at the center of research devoted to developing tumor vaccines and to expanding tumor-specific CTLS ex vivo for subsequent adoptive immunotherapy.

NK cells have unique cell-surface receptors that are important for immune surveillance of self-tissues and whose activities are mediated by binding of HLA class I antigen-presenting molecules that are found on most normal cells and tumors. Tumors that retain HLA class I expression evade NK cell-mediated cytotoxicity, but those that lose expression are no longer recognized by NK cells as "self" and are killed. Compounds that promote NK cell activation and adoptive immunotherapies that use allogeneic NK cells are active areas of preclinical and clinical investigation.

In certain embodiments, the anti-cancer agent is an antibody (e.g., a monoclonal antibody or mAb) or antigen-binding fragment thereof. In certain embodiments, the antibody blocks or enhances ligand-receptor interactions between cells (e.g., between a tumor cell and an immune cell, such as a T cell, a TAM, an MDSC, a DC, an NK cell, etc.). In certain embodiments, the antibody acts as agonists or antagonists of ligand-receptor interactions between cells (e.g., between a tumor cell and an immune cell, such as a T cell, a TAM, an MDSC, a DC, an NK cell, etc.). In certain embodiments, the antibody targets cellular destruction by antibody-dependent cellular cytotoxicity (ADCC). In certain embodiments, the antibody delivers conjugated drug payloads to specific target cells.

In certain embodiments, the anti-cancer agent is a genetically engineered lymphocyte that expresses conventional T cell receptors or chimeric antigen receptors (CARs), which can be used in an adoptive cell transfer immunotherapy. In certain embodiments, the genetically engineered lymphocyte is a T cell that expresses an antibody against a cancer associated antigen, wherein the antibody is linked or fused to a transmembrane and/or signaling domain of a CAR. Such T cells can be used for adoptive T-cell therapy.

In certain embodiments, the anti-cancer agent is a bi-specific T-cell Engager (BiTE) that comprises binding specificity regions from two antibodies fused into a single molecule, in order to directly bind CTLs to antigens on tumor cells to enhance tumor killing.

In certain embodiments, the anti-cancer agent is re-infused TILs expanded ex vivo, wherein the TILs are genetically engineered to express T-cell receptors (TCR) that are specific for unique tumor antigens. In certain embodiments, the tumor is cervical cancer, lymphoma, or leukemia. In certain embodiments, the anti-cancer agent further comprises an inhibitor of immune checkpoint, such as an anti-CTLA-4 antibody, an anti-PD-1 antibody, or an anti-PD-L1 antibody.

In certain embodiments, the anti-cancer agent is an allogeneic donor lymphocyte infusion (DLI), or allogeneic NK cell infusion.

In certain embodiments, the anti-cancer agent is adaptively transferred dendritic cells that have been primed by tumor-specific antigens prior to the adaptive transfer.

In certain embodiments, the anti-cancer agent is a vaccine comprising tumor-specific antigen, wherein the vaccine amplifies endogenous tumor-specific T cell response.

In certain embodiments, the mouse is homozygous or hemizygous for the IL-2 receptor gamma chain deficiency.

Another aspect of the invention provides a method of generating humanized immunodeficient non-obese diabetic mouse with patient-derived xenograft, the method comprising: (1) introducing, into an immunodeficient non-obese diabetic mouse, CD34$^+$ human hematopoietic stem cells (HSCs), wherein the mouse: (a) is homozygous for the scid mutation; and, (b) has an IL-2 receptor gamma chain deficiency; (2) inoculating said mouse with a human patient-derived xenograft (PDX), wherein said HSCs and said PDX are non-HLA matched.

Another aspect of the invention provides a method for xenogeneic stem cell engraftment in an immunodeficient non-obese diabetic mouse having a severe combined immunodeficiency, comprising: administering xenogeneic stem cells to the mouse.

Another aspect of the invention provides a method of predicting efficacy rank order for a plurality of anti-tumor agents for treating a tumor, the method comprising: (1) administering each one of the plurality of anti-tumor agents as single agent to a subject (non-HLA matched PDX) mouse (e.g., an NSG mouse), and determining efficacy, wherein the PDX represents the tumor; (2) comparing and/or ranking efficacy for each one of the plurality of anti-tumor agents, thereby predicting efficacy rank order for said plurality of anti-tumor agents for treating the tumor.

Another aspect of the invention provides a method of testing combination therapy for treating a tumor using two or more candidate agents, the method comprising: (1) administering said two or more candidate agents, either as single agent or as a combination, to a mouse of claim 1, and determining efficacy, wherein said PDX represents said tumor; (2) comparing efficacy for the combination and efficacy for the single agents, wherein a higher efficacy for the combination compared to the additive efficacy of the single agents is indicative that the combination is superior.

Another aspect of the invention provides a method to determine the efficacy and/or safety of a dosing regimen for treating a tumor using an agent, the method comprising: (1) administering said agent to a mouse of claim 1, wherein said PDX represents said tumor, and wherein said agent is administered according to said dosing regimen; (2) determining efficacy and/or safety.

It is contemplated that any one of the embodiments described herein, including those only described in the Examples and those only described under one aspect of the invention, can be combined with any one or more other embodiments unless explicitly disclaimed or inapplicable as one of skill in the art would understand.

BRIEF DESCRIPTION OF THE DRAWINGS

FIG. 3 shows hCD45$^+$ cells (%) in peripheral blood at 50 days post SKOV3 cancer cell inoculation.

FIGS. 4A-4C show growth curves for non-HLA matched tumors (BR0744, LG0977, and SA0209, respectively) in NSG vs. humanized NSG mice.

FIGS. 6A-6C show human lymphocyte percentage of the total infiltrating CD45$^+$ cells in the three non-HLA matched tumor PDX (BR0744, LG0977, and SA0209, respectively).

FIG. 10A-10C show that human T cells are present in the tumor tissue of the subject Hu-CD34 NSG™ non-HLA matched MDA-MB-231 PDX mice.

FIG. 14B shows mean tumor volume on Study Day 24 in the three groups. A similar experiment as the one in FIG. 14A was run and the result was shown in FIG. 14C.

Figure 15B:
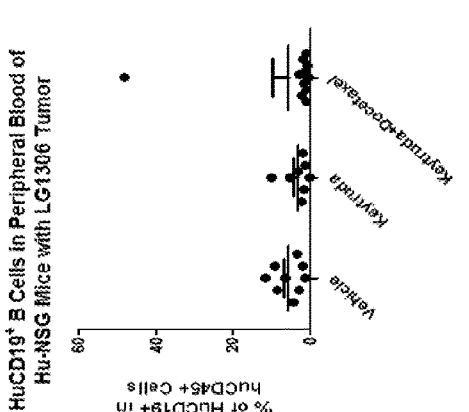
Figure 15A:
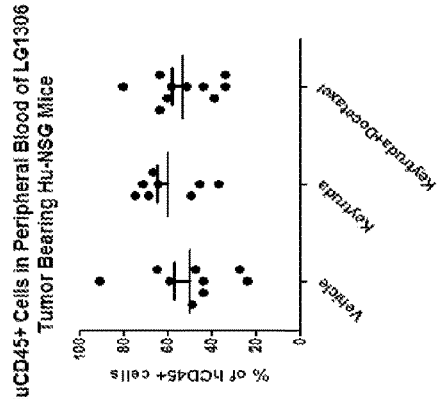
Figure 15D:
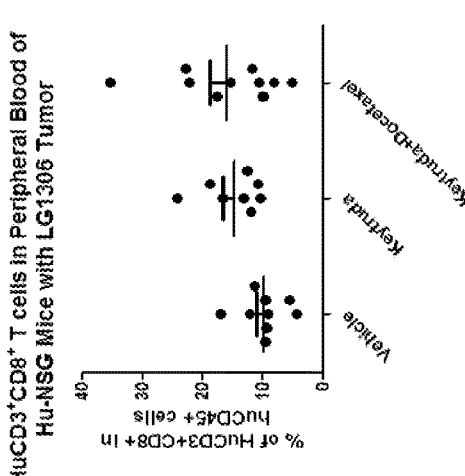
Figure 15C:
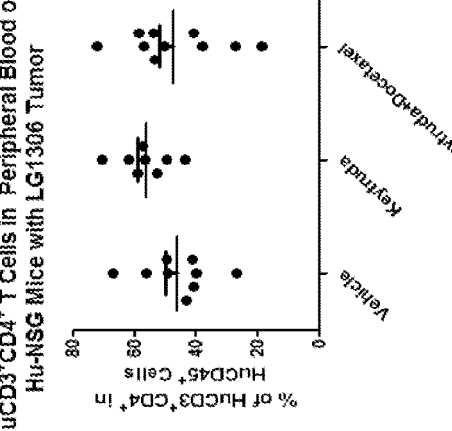
Figure 15I:
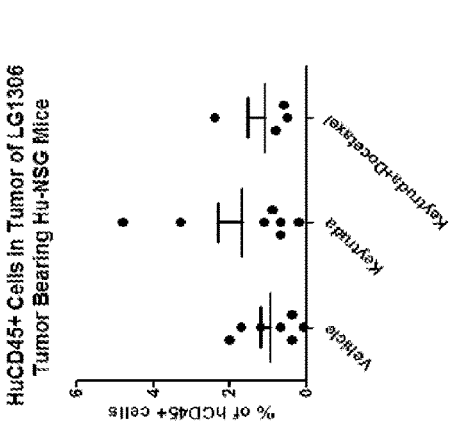
Figure 15K:
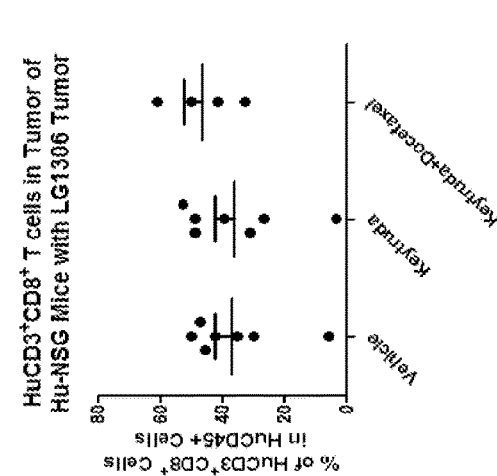
Figure 15J:
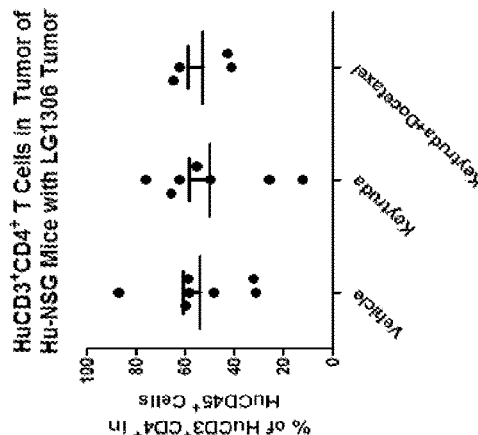

FIGS. 15A-15D show that human T cells (both CD3$^+$CD4$^+$ and CD3$^+$CD8$^+$) and B cells (CD19$^+$) are present in the peripheral blood of the subject Hu-CD34 NSG™ non-HLA matched LG1306 PDX mice. FIG. 15E-15H show that human T and B cells are present in the spleens of the subject Hu-CD34 NSG™ non-HLA matched LG1306 PDX mice. FIG. 15I-15K show that human T and B cells are present in the tumor tissue of the subject Hu-CD34 NSG™ non-HLA matched LG1306 PDX mice.

Figure 16:
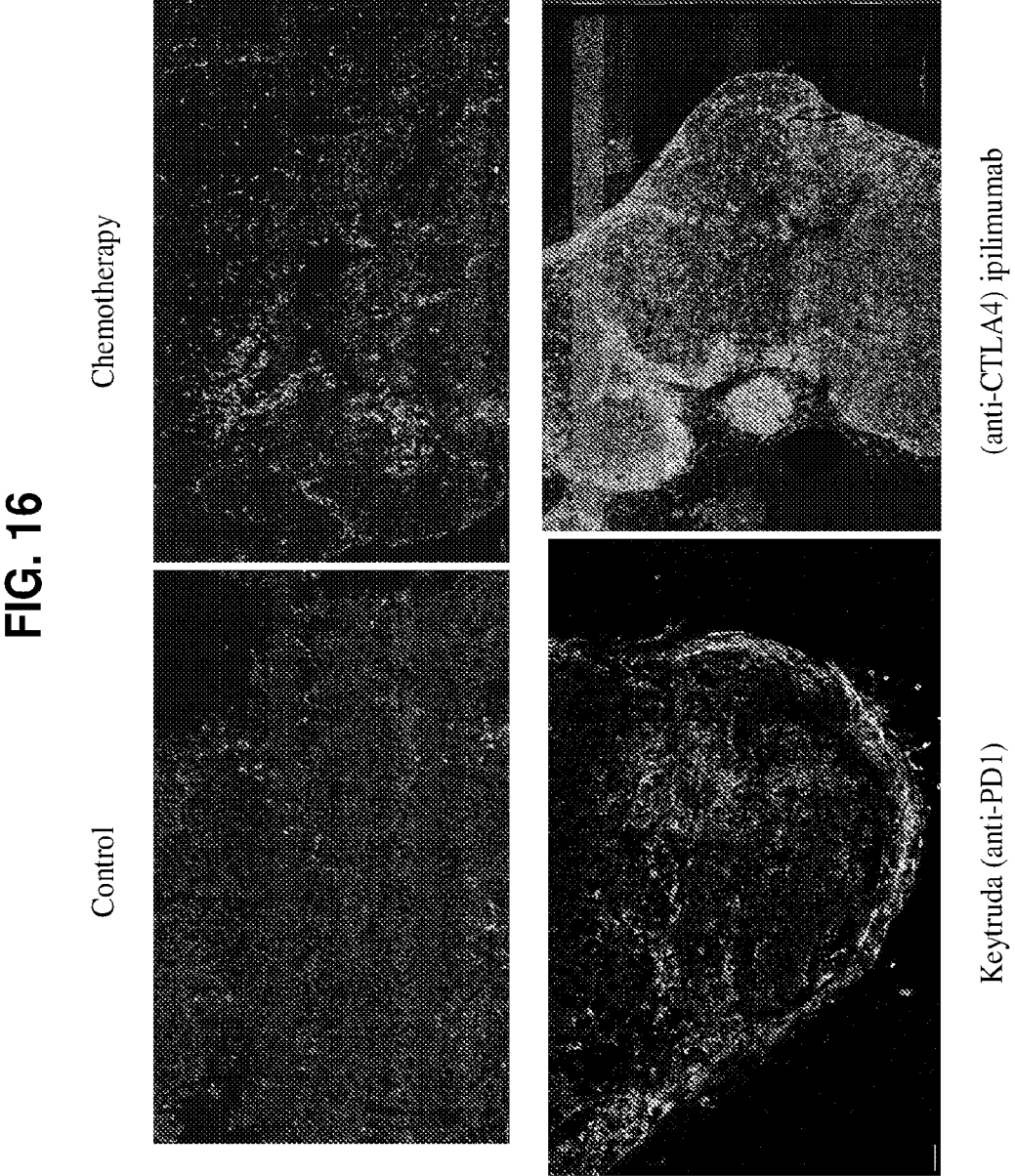

FIG. 16 shows immuno-staining for the presence of CD45$^+$CD8$^+$ infiltrating T cells in PDX samples treated by vehicle (control), chemotherapy alone, anti-PD1 (Keytruda), and anti-CTLA4 agent (ipilimumab). The data shows that anti-PD1 and anti-CTLA4 therapies led to strong presence of infiltrating T cells in the PDX tumors.

DETAILED DESCRIPTION OF THE INVENTION

1. Overview

The traditional approach to cancer treatment utilizes broad-acting chemical agents that are toxic to rapidly dividing cells, such as tumor/cancer cells. This chemotherapeutic approach can be successful but can be complicated by a wide array of off-target toxicities and has the risk of inducing drug resistance. Mammalian immune systems have developed a number of efficient, highly specific mechanisms for eliminating target cells, including cells that are infected with pathogens and those that have become cancerous. In response, tumor cells have developed their own suite of mechanisms for evading immunodetection. Hence, gaining a better understanding of the interaction between immune effector cells and tumors opens a new and promising avenue of treatment strategies that stimulate durable, immune-mediated tumor regression for clinical use. This class of new immuno-oncology treatment strategies are highly encouraging, yet further research in this field can benefit from the subject humanized, small animal model-based (e.g., mouse-based) in vivo testing platform that permits insights into a better biological understanding of human immune and tumor cell interactions, and enables preclinical testing of new therapies that have a higher likelihood for success when translated to clinical application.

The invention described herein is partly based on the surprising discovery that growth rate of the patient-derived xenograft (PDX) in the human CD34$^+$-engrafted NSG mice does not require complete HLA-type matching between the PDX and the engrafted human immune cells.

The invention described herein is also partly based on the surprising discovery that timing of cancer cell line engraftment, relative to humanization, has no significant impact on xenograft growth. On the other hand, timing of cancer cell line engraftment also has no significant effect on CD45$^+$ cell population.

Thus one aspect of the invention provides a humanized immunodeficient non-obese diabetic (NOD) mouse, wherein the mouse: (1) is homozygous for the scid mutation; (2) has an IL-2 receptor gamma chain deficiency; (3) is engrafted with CD34$^+$ human hematopoietic stem cells (HSCs); (4) is inoculated with a human patient-derived xenograft (PDX); wherein the HSCs and the PDX are non-HLA matched.

As used herein, "non-HLA matched" refers to not complete HLA-matched, including only partial HLA-match, or not HLA-matched. In certain embodiments, there is only partial HLA-match between the HSCs and the PDX. In certain embodiments, there is no HLA-match between the HSCs and the PDX.

In certain embodiments, the mouse is an NSG mouse, or a closely related derivative such as an NSGS mouse, an NSG-SGM3 mouse, or a human CD34$^+$ engrafted BLT-mouse.

The humanized mouse of the invention can be used in a broad spectrum of biological, medical, and clinical research, including cancer biology, immuno-oncology, regenerative medicine, human hematopoiesis, infectious diseases, transplantation, preclinical drug efficacy testing studies, and immunity and autoimmunity, just to name a few.

For example, the subject humanized mouse models can be used to study immune response in cancer therapy, treatment of infectious disease, gene therapy, and immunogenicity of large molecule drugs, etc.

The subject humanized mouse models can also be used in preclinical prediction studies, such that a patient-specific xenograft (such as a PDX from a cancer) can be studied in the subject mouse model, in the presence of engrafted human hematopoietic systems. The effect, safety (e.g., any associated side effect on immune system), and efficacy of any test compounds or drugs can be studied by administering such test compounds or drugs under one or more dosing regimens to the subject mouse model. This is particularly powerful in studying immuno-oncology or immuno-modulators, or any study involving the interaction between a diseased tissue (e.g., cancer, autoimmune disease) and the immune system.

The subject humanized mouse models can further be used to study any PDX in the presence of engrafted human hematopoietic system. This includes conducting tumor histology studies, omic studies or profiling (proteomic, genomic, metablomic, etc.). In certain embodiments, information concerning the PDX under study may be obtained from the Mouse Tumor Biology Database (MTB), which was designed to aid researchers in such areas as choosing experimental models, reviewing patterns of mutations in specific cancers, and identifying genes that are commonly mutated across a spectrum of cancers.

The subject humanized mouse models can also be used to study human immune system development and function, including development of humanized mouse models, analysis of innate immune cell function, examination of T cell homeostasis, and/or characteristics of the BLT (fetal thymus/fetal liver) mouse model.

With the general aspects of the invention described above, certain aspects or embodiments of the invention are further described in the sections below.

2. Definitions

Unless indicated otherwise, scientific and technical terms used herein are intended to have the meanings commonly understood by those of ordinary skill in the art. Such terms are found defined and used in context in various standard references illustratively including J. Sambrook and D. W. Russell, *Molecular Cloning: A Laboratory Manual*, Cold Spring Harbor Laboratory Press; 3rd Ed., 2001; F. M. Ausubel, Ed., *Short Protocols in Molecular Biology, Current Protocols;* 5th Ed., 2002; B. Alberts et al., *Molecular Biology of the Cell*, 4th Ed., Garland, 2002; D. L. Nelson and M. M. Cox, *Lehninger Principles of Biochemistry*, 4th Ed., W.H. Freeman & Company, 2004; Herdewijn, P. (Ed.), *Oligonucleotide Synthesis: Methods and Applications, Methods in Molecular Biology*, Humana Press, 2004; A.

Nagy, M. Gertsenstein, K. Vintersten, R. Behringer (Eds.) 2002, *Manipulating the Mouse Embryo: A Laboratory Manual*, 3$^{rd}$ edition, Cold Spring Harbor Laboratory Press, ISBN-10: 0879695919; and K. Turksen (Ed.), "Embryonic Stem Cells: Methods And Protocols in Methods," *Mol. Biol.*, 185:499, 2002, Humana Press; *Current Protocols in Stem Cell Biology*, ISBN: 9780470151808.

The singular terms "a," "an," and "the" are not intended to be limiting and include plural referents unless explicitly stated otherwise or the context clearly indicates otherwise.

The terms "express," "expression," "expressing" and "expresses" with reference to a gene or refer to transcription of the gene to produce a corresponding mRNA and/or translation of the mRNA to produce a functional corresponding encoded protein.

The term "immunodeficient non-human animal" refers to a non-human animal (e.g., mouse) characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA.

The term "immunodeficient mouse" refers to a mouse characterized by one or more of: a lack of functional immune cells, such as T cells and B cells; a DNA repair defect; a defect in the rearrangement of genes encoding antigen-specific receptors on lymphocytes; and a lack of immune functional molecules such as IgM, IgG1, IgG2a, IgG2b, IgG3 and IgA. Immunodeficient mice can be characterized by one or more deficiencies in a gene involved in immune function, such as Rag1 and Rag2 (Oettinger et al., *Science*, 248:1517-1523, 1990; and Schatz et al., *Cell*, 59:1035-1048, 1989) Immunodeficient mice may have any of these or other defects which result in abnormal immune function in the mice.

Particularly useful immunodeficient mouse strains are NOD.Cg-Prkdc$^{scid}$Il2rg$^{tml\ Wjl}$/SzJ, commonly referred to as NOD scid gamma (NSG) mice, described in detail in Shultz et al., *J. Immunol.*, 174:6477-6489, 2005; and NOD.Cg-Rag1$^{tmlMom}$Il2rg$^{tml\ Wjl}$/SzJ, Shultz et al., *Clin. Exp. Immunol.*, 154(2):270-284, 2008, commonly referred to as NRG mice.

The term "severe combined immune deficiency (SCID)" refers to a condition characterized by absence of T cells and lack of B cell function.

Common forms of SCID include: X-linked SCID which is characterized by gamma chain gene mutations in the IL2RG gene and the lymphocyte phenotype T($^-$) B($^+$) NK($^-$); and autosomal recessive SCID characterized by Jak3 gene mutations and the lymphocyte phenotype T($^-$) B($^+$) NK($^-$), ADA gene mutations and the lymphocyte phenotype T($^-$) B($^-$) NK($^-$), IL-7R alpha-chain mutations and the lymphocyte phenotype T($^-$) B($^+$) NK($^+$), CD3 delta or epsilon mutations and the lymphocyte phenotype T($^-$) B($^+$) NK($^+$), RAG1/RAG2 mutations and the lymphocyte phenotype T($^-$) B($^-$) NK($^+$), Artemis gene mutations and the lymphocyte phenotype T($^-$) B($^-$) NK($^+$), CD45 gene mutations and the lymphocyte phenotype T($^-$) B($^+$) NK($^+$).

A genetically modified mouse according to aspects of the present invention has the severe combined immunodeficiency mutation (Prkdc$^{scid}$), commonly referred to as the scid mutation. The scid mutation is well-known and located on mouse chromosome 16 as described in Bosma et al., *Immunogenetics*, 29:54-56, 1989. Mice homozygous for the scid mutation are characterized by an absence of functional T cells and B cells, lymphopenia, hypoglobulinemia and a normal hematopoetic microenvironment. The scid mutation can be detected, for example, by detection of markers for the scid mutation using well-known methods, such as PCR or flow cytometry.

A genetically modified mouse according to aspects of the present invention has an IL2 receptor gamma chain deficiency. The term "IL2 receptor gamma chain deficiency" refers to decreased IL2 receptor gamma chain. Decreased IL2 receptor gamma chain can be due to gene deletion or mutation. Decreased IL2 receptor gamma chain can be detected, for example, by detection of IL2 receptor gamma chain gene deletion or mutation and/or detection of decreased IL2 receptor gamma chain expression using well-known methods. In certain embodiments, the IL2 receptor gamma chain deficiency is a null mutation of the IL2 receptor gamma chain gene. In certain embodiments, the animal having IL2 receptor gamma chain deficiency is a homozygous mutant for the IL2 receptor gamma chain.

Genetically modified immunodeficient mice having the scid mutation, or an IL2 receptor gamma chain deficiency in combination with the scid mutation are provided according to aspects of the present invention. Genetically modified NOD scid gamma mice are provided according to aspects of the present invention.

The terms "NOD scid gamma" and "NSG" are used interchangeably herein to refer to a well-known immunodeficient mouse strain NOD.Cg-Prkdc*scid* NSG mice combine multiple immune deficits from the NOD/ShiLtJ background, the severe combined immune deficiency (scid) mutation, and a complete knockout of the interleukin-2 receptor gamma chain. As a result, NSG mice lack mature T, B and NK cells, and are deficient in cytokine signaling. NSG mice are characterized by lack of IL2R-γ (gamma c) expression, no detectable serum immunoglobulin, no hemolytic complement, no mature T lymphocytes, and no mature natural killer cells.

Genetically modified immunodeficient non-human animals (e.g., mice) having severe combined immunodeficiency or an IL2 receptor gamma chain deficiency in combination with severe combined immunodeficiency are provided according to aspects of the present invention.

Generation of a genetically modified immunodeficient non-human animal can be achieved by introduction of a gene targeting vector into a preimplantation embryo or stem cells, such as embryonic stem (ES) cells or induced pluripotent stem (iPS) cells.

The term "gene targeting vector" refers to a double-stranded recombinant DNA molecule effective to recombine with and mutate a specific chromosomal locus, such as by insertion into or replacement of the targeted gene.

The term "wild-type" refers to a naturally occurring or unmutated organism, protein or nucleic acid.

Optionally, genetically modified immunodeficient non-human animals (e.g., mice) of the present invention are produced by selective breeding. A first parental strain of non-human animal which has a first desired genotype may be bred with a second parental strain of non-human animal which has a second desired genotype to produce offspring which are genetically modified non-human animals having the first and second desired genotypes.

Genetically modified immunodeficient non-human animals of the present invention are preferably non-human mammals, particularly rodents, such as mice, rats or guinea pigs.

A genetically modified immunodeficient mouse having an IL2 receptor gamma chain deficiency in combination with the scid mutation provided according to aspects of the present invention may be an NSG mouse, an NSGS mouse, a human CD34⁺ HSC engrafted NSG/NSGS mouse, or a human CD34⁺ engrafted BLT-mouse.

The term "xenogeneic" is used herein with reference to a host cell or organism to indicate that the material referred to as "xenogeneic" is derived from another species than that of the host cell or organism.

The term "hematopoietic stem cells" as used herein refers to multipotent stem cells functional to give rise to an immune system. Hematopoietic stem cells from mice express c-Kit receptor. C-Kit receptor is well-known in the art, for example as described in Vandenbark et al., "Cloning and structural analysis of the human c-kit gene," Oncogene, 7(7): 1259-1266, 1992; and Edling & Hallberg, "c-Kit—a hematopoietic cell essential receptor tyrosine kinase," *Int. J. Biochem. Cell Biol.,* 39(11):1995-1998, 2007. Human hematopoietic stem cells express CD34. CD34 is a well-known protein, for example as described in Simmons et al., "Molecular cloning of a cDNA encoding CD34, a sialomucin of human hematopoietic stem cells," *J. Immunol.,* 148 (1):267-271, 1992.

According to aspects of the present invention, xenogeneic (e.g., human) hematopoietic stem cells are administered to a genetically modified immunodeficient non-human animal (e.g., mouse) of the present invention, wherein the xenogeneic hematopoietic stem cells differentiate into xenogeneic immune cells in the genetically modified immunodeficient non-human animal.

According to aspects of the present invention, human hematopoietic stem cells are administered to a genetically modified immunodeficient mouse of the present invention, wherein the human hematopoietic stem cells differentiate into human immune cells in the genetically modified immunodeficient mouse.

Hematopoietic stem cells for administration to a genetically modified immunodeficient animal can be obtained from any tissue containing HSC such as, but not limited to, umbilical cord blood, bone marrow, GM-CSF-mobilized peripheral blood and fetal liver.

Optionally, hematopoietic stem cells for administration to a genetically modified immunodeficient animal can be obtained as cells cultured in vitro prior to administration to expand the population of cells obtained from one or more tissues containing HSC such as, but not limited to, umbilical cord blood, bone marrow, GM-CSF-mobilized peripheral blood and fetal liver.

HSC can be administered into newborn animals by administration via various routes, such as, but not limited to, into the heart (intracardiac injection), liver (intrahepatic injection) and/or facial vein. HSC can be administered into adult animals by various routes, such as, but not limited to, administration into the tail vein, into the femur bone marrow cavity or into the spleen. In a further example, the HSC as fetal liver and/or fetal thymus can be engrafted under the renal capsule (e.g., as 1 mm³ cube organoids in BLT mouse).

Optionally, HSC are administered to a conditioned animal. Conditioning of a recipient animal in preparation for receipt of HSC is performed to deplete or suppress the HSCs and progenitor cells endogenous to the recipient animal prior to receipt of the xenogeneic HSCs. Conditioning of a recipient animal includes administration of radiation and/or one or more chemical agents effective to deplete or suppress the HSCs and progenitor cells endogenous to the recipient animal prior to receipt of the xenogeneic HSCs. Busulfan is a well-known example of a chemical agent effective to deplete or suppress the HSCs and progenitor cells endogenous to the recipient animal prior to receipt of the xenogeneic HSCs. Conditioning by radiation and/or one or more chemical agents effective to deplete or suppress the HSCs and progenitor cells endogenous to the recipient animal prior to receipt of the xenogeneic HSCs is performed according to well-known protocols to produce a conditioned animal.

Engraftment of xenogeneic HSC can be assessed by any of various methods, such as, but not limited to, flow cytometric analysis of cells in the animals to which the xenogeneic HSC are administered at one or more time points following the administration of HSC.

Exemplary methods for isolation of xenogeneic HSC, administration of the xenogeneic HSC to a host organism and methods for assessing engraftment thereof are described herein and in T. Pearson et al., *Curr. Protoc. Immunol.,* 81:15.21.1-15.21.21, 2008; Ito et al., *Blood,* 100:3175-3182, 2002; Traggiai et al., *Science,* 304:104-107, 2004; Ishikawa et al., *Blood,* 106:1565-1573, 2005; Shultz et al., *J. Immunol.* 174: 6477-6489, 2005; Holyoake et al., *Exp Hematol.,* 27(9):1418-1427, 1999, all incorporated by reference.

The HSCs administered are isolated from an original source material to obtain a population of cells enriched in HSCs. The isolated HSCs may or may not be pure.

In certain embodiments, HSCs are purified by selection for a cell marker, such as CD34.

In certain embodiments, administered human HSCs are a population of human cells in which CD34$^+$ cells constitute about 1-100% of total cells, although a population of human cells in which CD34$^+$ cells constitute fewer than 1% of total cells can be used. In certain embodiments, administered human HSCs are T cell depleted umbilical cord blood cells in which CD34$^+$ cells make up about 1-3% of total cells, lineage depleted umbilical cord blood cells in which CD34$^+$ cells make up about 50% of total cells, or CD34$^+$ positively selected cells in which CD34$^+$ cells make up about 90% of total cells.

The number of HSCs administered is not considered limiting with regard to generation of a xenogeneic immune system in an immunodeficient mouse. A single HSC can generate cells of an immune system. Thus, the number of administered HSCs is generally in the range of 1-10×10$^6$ HSCs where the recipient is a mouse, although more can be used. For other species, the number of cells can be adjusted if necessary using only routine experimentation.

In general, HSCs are present as a subpopulation of CD34$^+$ cells in a larger population of CD34$^+$. Thus, administration of a population of CD34$^+$ cells obtained from any tissue containing HSC such as, but not limited to, umbilical cord blood, bone marrow, GM-CSF-mobilized peripheral blood and fetal liver is administered to deliver the HSC subpopulation to the recipient animal to be engrafted. The number of CD34$^+$ cells obtained from any tissue containing HSC such as, but not limited to, umbilical cord blood, bone marrow, GM-CSF-mobilized peripheral blood and fetal liver administered to deliver the HSC subpopulation to the recipient animal to be engrafted is not limited and can be in the range of 1 cell-1 billion cells, such as 1 cell-500 million cells, 1 cell-100 million cells, 1 cell-10 million cells, 1 cell-5 million cells, 1 cell-1 million cells, 1 cell-500,000 cells, 1 cell-100,000 cells, 1 cell 50,000 cells, 1 cell-10,000 cells, 1 cell-1,000 cells, of such CD34$^+$ cells. Further, the number of CD34$^+$ cells administered is in the range of 100 cells-10 million cells, 100 cells-5 million cells, 100 cells-1 million cells, 100 cells-500,000 cells, 100 cells-100,000 cells, 100 cells-50,000 cells, 100 cells-10,000 cells or 100 cells-1,000 cells. Still further, the number of CD34$^+$ cells administered is in the range of 1000 cells-10 million cells, 1000 cells-5 million cells, 1000 cells-1 million cells, 1000 cells-500,000 cells, 1000 cells-100,000 cells, 1000 cells-50,000 cells or 1000 cells-10,000 cells.

Engraftment is successful where xenogeneic HSCs and cells differentiated from the HSCs in the recipient animal are detected at a time when the majority of any administered non-HSC have degenerated. The hallmark of successful human HSC engraftment is multi-lineage human immune cell differentiation and homing to bone marrow, thymus, spleen, and PBL, etc. NSG mice support multi-lineage engraftment and immune cell homing into nearly all of the appropriate organs and tissues. The full range of the human immune cell populations detected in hu-CD34 NSG mice are summarized in Ishikawa et al. (*Blood,* 106(5): 1565-1573, 2005); and Tanaka et al. (*J. Immunol.,* 188(12): 6145-6155, 2012).

Detection of differentiated HSC cells can be achieved by detection of xenogeneic DNA in the recipient animal or detection of intact xenogeneic HSCs and cells differentiated from the HSCs, for example. Serial transfer of CD34$^+$ cells into a secondary recipient and engraftment of a xenogeneic hematopoietic system is a further test of HSC engraftment in the primary recipient. Engraftment can be detected by flow cytometry as 0.05% or greater xenogeneic CD45$^+$ cells in the blood at 10-12 weeks after administration of the HSC.

Methods are provided according to aspects of the present invention which include delivery of xenogeneic stem cell factor (SCF) to the xenogeneic hematopoietic stem cells in the immunodeficient animals. The SCF may be delivered acutely or chronically to the animals. According to aspects of the present invention, the immunodeficient non-human animals may further include a transgene encoding a xenogeneic SCF operably linked to a promoter. In a further option, where the animals express the xenogeneic SCF, the animals are not conditioned by administration of a radiomimetic agent prior to administering the xenogeneic stem cells.

Methods for identifying modulators of an immune system response according to aspects of the present invention include providing a non-human genetically modified immunodeficient animal; administering xenogeneic hematopoietic stem cells to the non-human genetically modified immunodeficient animal, wherein the xenogeneic hematopoietic stem cells differentiate to produce xenogeneic immune cells in the non-human genetically modified immunodeficient animal; administering an immune system stimulator to the animal; administering a test compound to the animal; assaying a response of the xenogeneic immune cells to the immune system stimulator; and comparing the response to a standard to determine the effect of the test compound on the response of the xenogeneic immune cells to the stimulator, wherein an effect of the test substance identifies a modulator of the xenogeneic immune system in the animal.

A test compound used in a method of the present invention can be any chemical entity, illustratively including a synthetic or naturally occurring compound or a combination of a synthetic or naturally occurring compound, a small organic or inorganic molecule, a protein, a peptide, a nucleic acid, a carbohydrate, an oligosaccharide, a lipid or a combination of any of these.

A sample as used herein can be a sample obtained from a non-human animal, illustratively includes spleen, bone marrow, blood, blood plasma and blood serum.

Optionally, particular cell populations of the immune system are assayed, such as dendritic cells, plasmacytoid dendritic cells, myeloid dendritic cells, mast cells, monocytes/macrophages, natural killer cells, neutrophils, basophils and eosinophils, T lymphocytes (CD3⁺CD4⁺ or CD3⁺ CD8⁺ T cells), B lymphocytes (e.g., CD19⁺ B cells).

Isolated bone marrow cells of genetically modified immunodeficient non-human animals having an engrafted human immune system are provided by the present invention. Isolated bone marrow cells of genetically modified immunodeficient non-human animals having an engrafted human immune system are provided by the present invention.

Isolated cells of genetically modified immunodeficient non-human animals are provided by the present invention. Such isolated cells can be cultured in vitro for use in various assays. For example, such isolated cells are useful as controls in assays for assessment of a test substance to determine the activity of the test substance. In a further example, such isolated bone marrow cells are useful to determine the activity of the test substance on activity of the immune system.

Immunoassay methods can be used to assay a target analyte or an indicator of immune cell response in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, *Antibodies: A Laboratory Manual*, Cold Spring Harbor Laboratory Press, 1988; F. Breitling and S. Dubel, *Recombinant Antibodies*, John Wiley & Sons, New York, 1999; H. Zola, *Monoclonal Antibodies: Preparation and Use of Monoclonal Antibodies and Engineered Antibody Derivatives, Basics: From Background to Bench*, BIOS Scientific Publishers, 2000; B. K. C. Lo, *Antibody Engineering: Methods and Protocols, Methods in Molecular Biology*, Humana Press, 2003; F. M. Ausubel et al., Eds., *Short Protocols in Molecular Biology, Current Protocols*, Wiley, 2002; S. Klussman, Ed., *The Aptamer Handbook: Functional Oligonucleotides and Their Applications*, Wiley, 2006; Ormerod, M. G., *Flow Cytometry: A Practical Approach*, Oxford University Press, 2000; Givan, A. L., *Flow Cytometry: First Principles*, Wiley, New York, 2001; Gorczyca, W., *Flow Cytometry in Neoplastic Hematology: Morphologic-Immunophenotypic Correlation*, Taylor & Francis, 2006; Crowther, J. R., *The ELISA Guidebook (Methods in Molecular Biology)*, Humana Press, 2000; Wild, D., *The Immunoassay Handbook,* 3rd Edition, Elsevier Science, 2005; and J. Sambrook and D. W. Russell, *Molecular Cloning: A Laboratory Manual*, Cold Spring Harbor Laboratory Press, 3rd Ed., 2001.

Antibodies and methods for preparation of antibodies are well-known in the art. As used herein, the terms "antibody" and "antibodies" encompass monoclonal antibodies, polyclonal antibodies, bispecific antibodies, multispecific antibodies, human antibodies, humanized antibodies, chimeric antibodies, camelized antibodies, single domain antibodies, single-chain Fvs (scFv), single chain antibodies, disulfide-linked Fvs (sdFv), and anti-idiotypic (anti-Id) antibodies and antigen-binding fragments of any of the above. In particular, antibodies include immunoglobulin molecules and immunologically active fragments of immunoglobulin molecules, i.e., molecules that contain an antigen binding site. Immunoglobulin molecules are of any type (e.g., IgG, IgE, IgM, IgD, IgA and IgY), class (e.g., IgG1, IgG2, IgG3, IgG4, IgA1 and IgA2), or subclass.

As used herein, the terms "antibody fragment" and "antigen-binding fragment" defines a fragment of an antibody that immunospecifically binds to a target analyte. Antibody fragments may be generated by any technique known to one of skill in the art. For example, Fab and F(ab')2 fragments may be produced by proteolytic cleavage of immunoglobulin molecules, using enzymes such as papain (to produce Fab fragments) or pepsin (to produce F(ab')2 fragments). Antibody fragments are also produced by recombinant DNA technologies.

Antibodies, antigen-binding fragments, methods for their generation and methods for screening of generated antibodies for substantially specific binding to an antigen are known in the art and such antibodies, antigen binding fragments and methods are described in further detail, for instance, in *Antibody Engineering*, Kontermann, R. and Dubel, S. (Eds.), Springer, 2001; Harlow, E. and Lane, D., *Antibodies: A Laboratory Manual*, Cold Spring Harbor Laboratory Press, 1988; F. Breitling and S. Dubel, *Recombinant Antibodies*, John Wiley & Sons, New York, 1999; H. Zola, *Monoclonal Antibodies: Preparation and Use of Monoclonal Antibodies and Engineered Antibody Derivatives, Basics: From Background to Bench*, BIOS Scientific Publishers, 2000; Ausubel, F. et al., (Eds.), *Short Protocols in Molecular Biology*, Wiley, 2002; J. D. Pound (Ed.) *Immunochemical Protocols, Methods in Molecular Biology*, Humana Press, 2nd ed., 1998; B. K. C. Lo (Ed.), *Antibody Engineering: Methods and Protocols, Methods in Molecular Biology*, Humana Press, 2003; and Kohler, G. and Milstein, C., *Nature*, 256:495-497 (1975). Antibodies for target analytes, such as toll-like receptor 4 or indicators of innate immune cell response, can be produced in animals, synthesized, produced by recombinant methods and/or obtained commercially.

Detecting binding between a target analyte present in a sample and a binding partner is achieved by any of various methods known in the art, illustratively including detection of a detectable label directly or indirectly attached to the target analyte or the binding partner. The term "detectable label" refers to a material capable of producing a signal indicative of the presence of the detectable label by any appropriate method illustratively including spectroscopic, optical, photochemical, biochemical, enzymatic, electrical and/or immunochemical. Examples of detectable labels illustratively include a fluorescent moiety, a chemiluminescent moiety, a bioluminescent moiety, an electron dense particle, a magnetic particle, an enzyme, a substrate, a radioisotope and a chromophore.

The identity of a particular detectable label or labels used depends on the detection process used. Such detection processes are incorporated in particular assay formats illustratively including ELISA, Western blot, immunoprecipitation, immunocytochemistry, immuno-fluorescence assay, liquid chromatography, flow cytometry, other detection processes known in the art, or combinations thereof.

A binding assay can incorporate a binding partner attached to a support. A support with attached binding partner used in a binding assay can be solid or semi-solid and can be any of various materials such as glass, silicon, paper, a synthetic or naturally occurring polymer, such as polystyrene, polycarbonate, polypropylene, PVDF, nylon, cellulose, agarose, dextran, and polyacrylamide or any other material to which a binding partner can be stably attached for use in a binding assay.

A support used can include functional groups for binding to binding partners, such as, but not limited to carboxyl, amine, amino, carboxylate, halide, ester, alcohol, carbamide, aldehyde, chloromethyl, sulfur oxide, nitrogen oxide, epoxy and/or tosyl functional groups. Attachment of binding partners to a support is achieved by any of various methods, illustratively including adsorption and chemical bonding. In one example, 1-Ethyl-343-dimethylaminopropyl carbodiimide hydrochloride, EDC or EDAC chemistry, can be used to attach binding partners to particles. The binding partners can be bonded directly or indirectly to the material of the support, for example, via bonding to a coating or linker disposed on the support. Functional groups, modification thereof and attachment of a binding partner to a support are known in the art, for example as described in Fitch, R. M., Polymer Colloids: *A Comprehensive Introduction*, Academic Press, 1997.

Such supports can be in any of a variety of forms and shapes including, but not limited to, microtiter plates, microtiter wells, pins, fibers, beads, slides, silicon chips and membranes such as a nitrocellulose or PVDF membrane.

Any of various spectroscopy methods can be used to assay a target analyte, such as toll-like receptor 4 or an indicator of innate immune cell response, according to aspects of the present invention, including, but not limited to, gas chromatography, liquid chromatography, ion mobility spectrometry, mass spectrometry, liquid chromatography-mass spectrometry (LC-MS or HPLC-MS), ion mobility spectrometry-mass spectrometry, tandem mass spectrometry, gas chromatography-mass spectrometry, matrix-assisted desorption ionization time-of-flight (MALDI-TOF) mass spectrometry, surface-enhanced laser desorption ionization (SELDI) and nuclear magnetic resonance spectroscopy, all of which are well-known to the skill artisan.

Optionally, spectrometric analysis is used to assay a sample for a target analyte such as toll-like receptor 4 or an indicator of innate immune cell response. Mass analysis can be used in an assay according to aspects of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., *Clin Chem.*, 48(8):1296-1304, 2002; Hortin, G. L., *Clinical Chemistry*, 52: 1223-1237, 2006; A. L. Burlingame, et al. (Eds.), *Mass Spectrometry in Biology and Medicine*, Humana Press, 2000; and D. M. Desiderio, *Mass Spectrometry of Peptides*, CRC Press, 1990.

3. The Humanized Tumor-Bearing NSG Mice

The Jackson Laboratory NSG mice (NOD.Cg-Prkdc$^{scid}$ Il2rg$^{tm1Wjl}$/SzJ, Stock No. 005557) are also commonly known as NOD scid gamma; NSG; NOD-scid IL2Rgamma$^{null}$; and NOD-scid IL2Rg$^{null}$. They combine the features of the NOD/ShiLtJ background (Jackson Laboratory Stock No. 001976), the severe combined immune deficiency mutation (scid), and IL2 receptor gamma chain deficiency. As a result, The NSG mice lack mature T cells, B cells (and thus does not generate mouse antibodies), and functional NK cells, has no complement system, and are deficient in cytokine signaling, leading to better engraftment of human hematopoietic stem cells (HSCs) and peripheral-blood mononuclear cells (PBMCs) than any other published mouse strain. The NSG mice also has defective macrophages and dendritic cells. Recent publications have demonstrated this strain's outstanding utility in the studies of islet transplantation, hematopoietic stem cells and cancer stem cells.

Specifically, the NSG mice do not express the Prkdc gene nor the X-linked Il2rg gene. NSG mice are viable, fertile, normal in size and do not display any gross physical or behavioral abnormalities. Histological examination of lymphoid tissues reveals absence of lymphoid cells and some cystic structures in the thymus, an absence of follicles in the spleen and markedly diminished celluarity of lymph nodes. NSG mice are deficient in mature T- and B-lymphocytes, serum Ig is not detectable and natural killer (NK) cell cytotoxic activity is extremely low. These mice are resistant to lymphoma development even after sublethal irradiation treatment. These mutant mice have been shown to readily support engraftment of human CD34$^+$ hematopoietic stem cells and represent a superior, long-lived (median survival is over 89 weeks) model suitable for studies employing xenotransplantation strategies.

The NSG mice carry the true null interleukin-2 receptor gamma chain mutation, as opposed to other strains that express a truncated interleukin-2 receptor gamma chain (see Ohbo et al., *Blood*, 87:956-967, 1996). The NSG mice are available to non-profit research institutions under a material transfer agreement (MTA), and the Jackson Laboratory distributes NSG mice under an agreement with the NIH.

To create the subject humanized NSG mouse (HU-NSG™), hematopoietic stem cells, such as the human CD34$^+$ HSCs, are introduced into the Jackson Laboratory NSG mice by, for example, tail vein injection, intracardiac injection, or intrahepatic injection. The HSCs can be introduced into about 2-, 3-, or 4-week old NSG mice. Typically, 25-gauge needles can be used for tail vein injection. Smaller gauge needles can also be used, with potentially increased shearing of the cells in the inocula.

Alternative sites for delivery of HSCs include the retroorbital venous sinus, the bone marrow cavity itself, and the spleen. Injection into the retroorbital sinus is easier to perform, but more invasive, than using the tail vein, and it requires the recipient mouse to be anesthetized. The homing of stem cells to the marrow is dependent on molecules such as stromal-derived factor 1 and stem cell factor that guide the stem cells from the peripheral blood to the marrow cavity. Therefore, delivery of the stem cells into the circulation (or orthotopically into the marrow) increases the likelihood that the cells will establish residence in the bone marrow of the new host.

Optionally, just prior to HSCs introduction, the NSG mice are exposed whole- or total-body irradiation (TBI) for myeloablation, which can be achieved by placing the NSG mice in specifically designed irradiators, with a dose of whole-body gamma irradiation designed to causes the animals to become either transiently or chronically immuno-suppressed.

Successful survival of the human immune system in the NSG mice may require suppression of the host's immune system in some manner to prevent HVG (host-vs-graft) rejections. In addition to suppressing the host's immune system, irradiation also helps deplete the bone marrow niche of host progenitor cells, thereby allowing space for engraftment of donor stem cells. For NSG mice, this preparation is commonly accomplished through whole-body gamma irradiation. Irradiators may vary in size depending on their intended use. Small irradiators (for example, the Mark-I irradiator from J L Shepherd and Associates, San Fernando, CA) are the size of a refrigerator and commonly are used to irradiate both cells and a small number of mice. In contrast, one commonly used larger (6600 lb) gamma irradiator (the Gammacell-40, MDS Nordion, Ottawa, ON) can be used to irradiate several dozen mice at once. Animals are generally irradiated for short periods of time (less than 15 min). The amount of time spent inside the irradiator varies depending on the radioisotope decay charts, amount of irradiation needed, and source of ionizing energy (that is, X-rays versus gamma rays, for which a cesium or cobalt source is needed). Larger irradiators, such as Clinac 4/80 linear accelerator (Varian Medical Systems, Palo Alto, CA) may also be used if necessary. In general, the mice need not be anesthetized for irradiation.

The myeloablative irradiation dose is usually 700 to 1300 cGy, though in some embodiments, lower doses such as 1-100 cGy (e.g., about 2, 5, or 10 cGy), or 300-700 cGy may be used. It can be either cesium- or X-ray irradiation.

In certain embodiments, female NSG mice are surgically implanted with human thymus and liver fragments and injected with donor-matched human CD34$^+$ hematopoietic stem cells (humanized BLT NSG-mice). Such humanized BLT-mice (hu-BLT) have the most functional immune system of any current humanized mouse model, and offer distinct advantages and improved performance in certain studies, such as mucosal-based immune responses.

In certain embodiments, instead of using NSG mice for humanization, the NSGS or NSG-SGM3 mice (NOD.Cg-Prkdc$^{scid}$ Il2rg$^{tm1Wjl}$ Tg(CMV-IL3,CSF2,KITLG)1Eav/MloySzJ, Jackson Laboratory Stock No. 013062, also commonly known as NOD-scid IL2Rgnull-3/GM/SF) can be used. This is a multi-allelic mouse line combines an immunodeficient environment with the presence of several transgenic human cytokines supportive of human myeloid cell expansion, and represents an especially useful model for the hosting of xenografts. In particular, these mice harbor three transgenes, human interleukin-3 (IL-3), human granulocyte/macrophage-stimulating factor (GM-CSF), and human Steel factor (SF) gene, each driven by a human cytomegalovirus promoter/enhancer sequence. These mice are maintained on the NSG (NOD.Cg-Prkdc$^{scid}$ Il2rg$^{tm1Wjl}$/SzJ) mice background, and constitutively produce 2-4 ng/mL serum levels of human IL-3, GM-CSF, and SF. The Il2rg$^{-/-}$ specific NOD.SCID background supports human and murine hematopoietic cell engraftment, and suppresses human erythropoiesis, enhances human myelopoiesis, and reduces human B-lymphopoiesis in mice after transplant of human bone marrow or fetal liver cells.

In certain embodiments, the mouse is engrafted with human peripheral blood mononuclear cells, e.g., the hu-PBMC NSG™ mouse (or PBMC humanized mouse).

For simplicity, in certain embodiments, the various NSG or NSG derived mouse strains may be collectively referred to as NSG mouse.

In certain embodiments, the human CD34$^+$ HSCs are introduced into NSG mice (or NSGS mice, or BLT-NSG mice) when the mice are around 3 weeks of age, and mature human B cells appear around week-12, and mature human T cells appear around week-15.

In certain embodiments, human CD34$^+$ engrafted NSG mice (or NSGS mice, or BLT-NSG mice) have at least about 20%, 25%, 30% or more human CD45$^+$ cells in the peripheral blood of the mice about 12 weeks post HSCs engraftment.

To create the subject humanized NSG mice (or NSGS mice, or BLT-NSG mice) with patient-derived xenograft (PDX), the NSG mice (or NSGS mice, or BLT-NSG mice) repopulated by human CD34$^+$ HSCs are injected with an appropriate amount of patient-derived cells, such as 1-10× 10$^6$ human cancer cells. The human origin of the cancer cells can be verified by Ki67 staining. In certain embodiments, the PDX is introduced into the mice at about 2 weeks post HSCs engraftment. In certain embodiments, the PDX is introduced into the mice at about 1, 2, 3, 4, 5, 6, 7, 8, 9, 10, 11, 12, 13, 14, 15 weeks post HSCs engraftment. In certain embodiments, the PDX is introduced into the mice before the engrafted human immune cells (e.g., human B- or T-cells or NK cells) appear.

In certain embodiments, the HLA type of the PDX does not match the HLA type of the donor human HSCs.

EXAMPLES

Any patents or publications mentioned in this specification are incorporated herein by reference to the same extent as if each individual publication is specifically and individually indicated to be incorporated by reference.

The non-human animals (e.g., mouse), compositions, and methods of the present invention described herein are presently representative of certain illustrative embodiments, exemplary embodiments, and are otherwise not intended as limitations on the scope of the invention. Changes therein and other uses will occur to those skilled in the art. Such changes and other uses can be made without departing from the scope of the invention as set forth in the claims.

Example 1 Mice

NOD.Cg-Prkdc$^{scid}$ Il2rg$^{tm1\ Wjl}$/SzJ (NOD-scid IL2rγ$^{null}$, NSG) mice were obtained from colonies developed and maintained at The Jackson Laboratory (Bar Harbor, ME). All animals were housed in a specific pathogen free facility, in microisolator cages, and given autoclaved food and maintained on sulfamethoxazole-trimethoprim medicated water (Goldline Laboratories, Ft. Lauderdale, Fla.) and acidified autoclaved water on alternating weeks.

Example 2 Engraftment of Mice with Human Hematopoietic Stem Cells (HSCs)

Groups of 24 to 72 hour-old (newborn) NSG mice are irradiated with 100 cGy as described in Pearson et al. (*Curr. Protoc. Immunol.* 81:15.21.1-15.21.21, 2008). Irradiated mice are injected with CD3 T cell-depleted human umbilical cord blood (UCB) containing 3×10$^4$ CD34$^+$ hematopoietic stem cells (HSC) in a 25-50 µL volume via intracardiac injection as described in Brehm et al. (*Clinic. Immunol.* 135(1):84-98, 2010). After 12 weeks, flow cytometry analyses of the blood of HSC recipients quantifies the engraftment of the human immune system. For experimental studies only mice with >20% peripheral human CD45$^+$ cells and >5% human CD3$^+$ T cells are used.

Similarly, sub-lethally irradiated newborn NSG mice can also be injected with CD3 T cell-depleted human umbilical cord blood (UCB) containing 3×10$^4$ CD34$^+$ hematopoietic stem cells (HSC) via intrahepatic injection or through facial vein injection as described in Brehm et al. (*Clinic. Immunol.*, 135(1):84-98, 2010).

Furthermore, groups of about 3-weeks old NSG mice can be subject to whole-body sublethal irradiation at a dose of about 200 to 1300 cGy, before 0.2-1×10$^6$CD34$^+$ HSCs are injected via lateral tail vein using standard techniques. For example, each animal is weighed before injection, and up to about 1% of the animal's body weight in volume can be administered per injection. Prior to injection, warm animals for 5-10 minutes (e.g., in a commercially available warming box, or under an overheard heat lamp, or using a warm water circulating pad placed under the cage) to dilate the veins. Then lightly anesthetize animals are positioned on their side, on a rechargeable heat pack or circulating warm water pad to keep them warm during anesthesia. Then a small gauge (28-30) needle is inserted, bevel up, into the vein towards the direction of the animal head, trying to keep the needle and syringe parallel to the tail. The needle should advance smoothly into the vein. After injection, the animals are to cage and observed for 5-10 minutes to make sure that bleeding has not resumed.

For the BLT (bone marrow/liver/thymus) mouse model, about 1 mm$^3$ cubes of fetal liver and fetal thymus are implanted as organoids into the host NSG mouse, which has previously been subject to about 200 cGy of whole-body irradiation. Then about 0.2-1×10$^6$ CD34$^+$HSCs are injected via lateral tail vein using standard techniques. The BLT mouse model allows robust and consistent xenograft (e.g., human) immune system development, comprising multiple hematopoietic lineages; exhibits sustained, high level T cell development; and the T cells are educated on autologous thymic tissues. Such mouse model typically has detectable T and B cell responses to viral infection (e.g., EBV and HIV).

In any of the suitable humanized mouse models, such as in the humanized NSG mice, patient-derived xenograft (PDX) or cancer cell line is inoculated at specific time points, such as 2 or 12 weeks post human CD34$^+$ cell injection. The xenografts are allowed to grow, e.g., for about 7 weeks, with body weight and tumor volume monitored frequently (e.g., twice per week).

Peripheral blood from the mice may be collected at the end of the study, for analyzing the extent of human CD45$^+$ donor cell engraftment. Preferably, human CD45$^+$ donor cells must reach at least about 20-30% in the peripheral blood.

Figure 1:
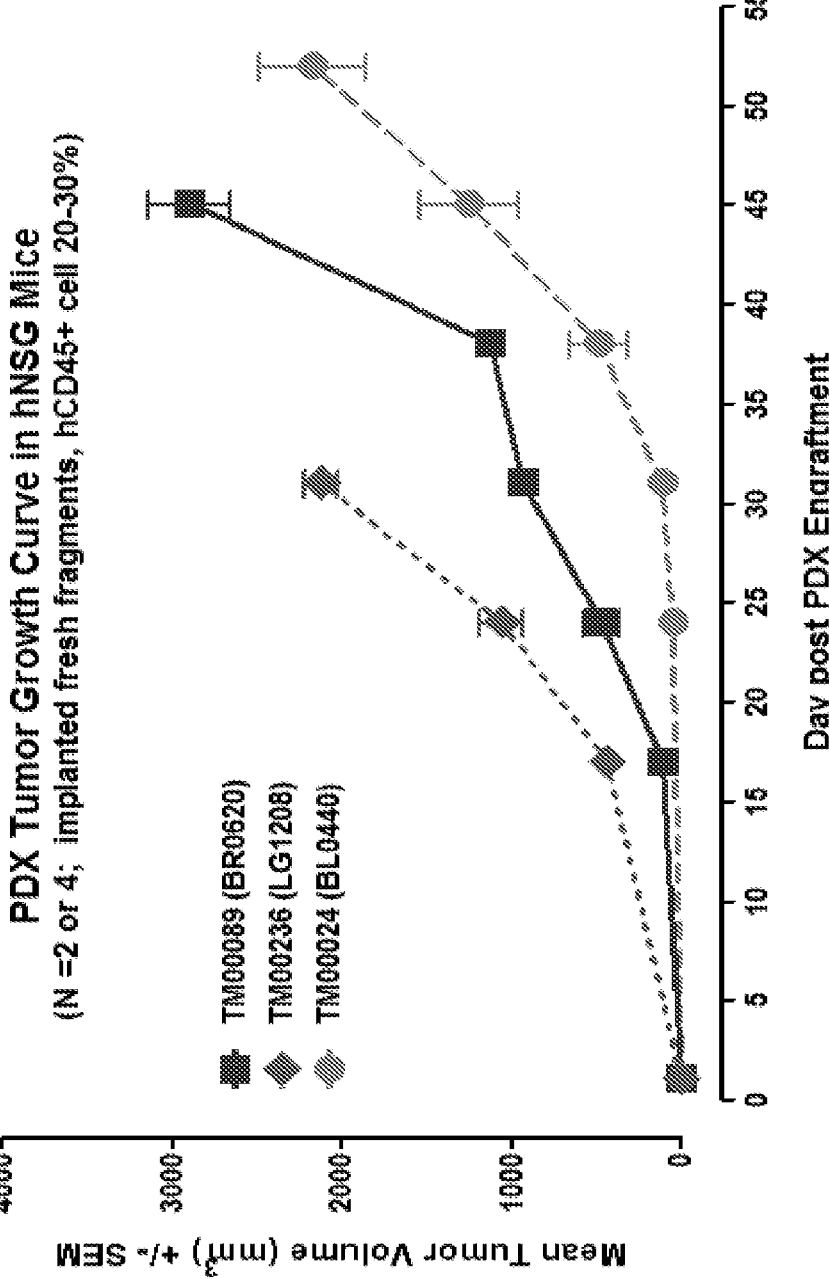
FIG. 1 shows growth curve for non-HLA matched tumors in humanized NSG mouse.

Example 3 Recapitulation of Expected PDX Growth Rates does not Require HLA-Type Matching Humanization of the NSG mouse were performed substantially as described above in Example 2. Briefly, groups of about 3 weeks old NSG mice were subject to whole-body irradiation (about 200 cGy) before about 0.2-1×10$^6$ CD34$^+$ HSCs are injected via lateral tail vein using standard techniques. PDX xenografts using three different cancer samples (breast cancer cells BR0620, lung cancer cells LG1208, and bladder cancer cells BL0440) were implanted subcutaneously into a subject humanized NSG mouse model—i.e., hu-CD34 NSG mice with established and functionally mature human immune cells derived from an HLA-mismatched human HSC donor, and the growth of the PDX engraftments were monitored for up to about 55 days post PDX engraftment. All three tumors showed robust growth and no obvious indication of rejection (FIG. 1).

The results show that HLA-type matching is not required to recapitulate expected PDX growth rate in the subject humanized NSG mouse model.

Example 4 Temporal Evaluation of PDX Engraftment on Tumor Growth in Hu-CD34 NSG™ Mice To evaluate any temporal effect on PDX xenograft tumor growth in non-HLA matched humanized hCD34$^+$ NSG mouse, about 5×10$^6$ human SKOV3 ovarian cancer cells were inoculated either 2 or 12 weeks post non-HLA matched human CD34$^+$ cell injection into the NSG mouse, according to a procedure substantially as described in Examples 2 and 3 above. The xenografts were allowed to grow for about 7 more weeks, with body weight and tumor volume monitored twice per week. Peripheral blood from the mice was collected at the end of the study, for analyzing the extent of human CD45$^+$ donor cell engraftment. Average results from two groups of 7 mice each (2 weeks vs. 12 weeks) were shown in FIG. 2.

Figure 2:
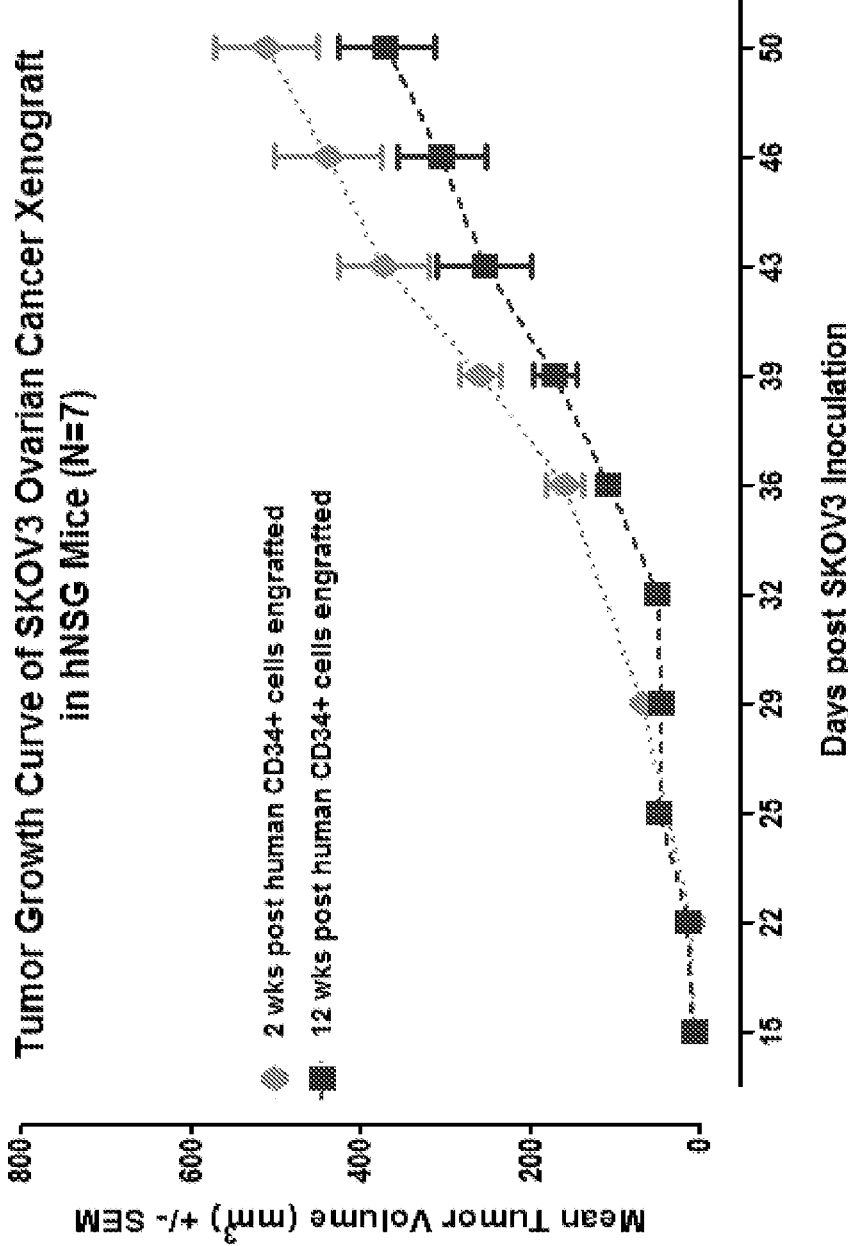
FIG. 2 shows the growth curve of the non-HLA matched SKOV3 ovarian cancer xenograft in humanized NSG mouse (n=7).

At 2 weeks post-engraftment, human immunity has not yet developed. Indeed, mature human T and B cells require at least 12 weeks to become detectable in the PBL of hu-CD34 NSG mice. In the tumor engraftment studies, however, tumor take was 100% in both groups (N=7 for both) and the increase in tumor volume over time in the 2 week group slightly outpaced the 12 week group (FIG. 2).

The results showed that there is no significant difference between the two groups of mice, suggesting that timing of cancer cell line engraftment, relative to humanization, has no significant (if any) impact on growth of SKOV3 ovarian cancer cells.

Figure 3:
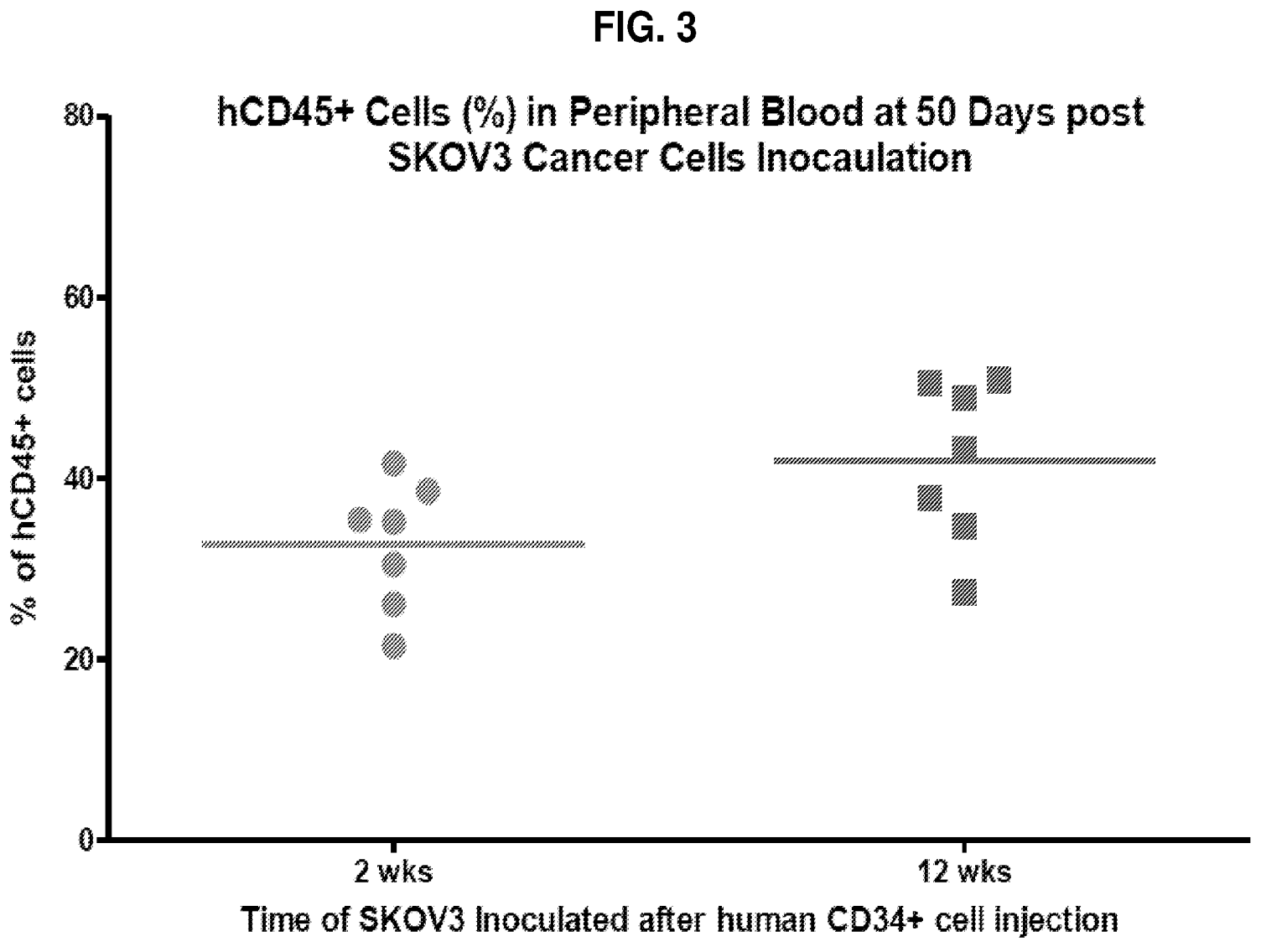

The mice were tested for human hematopoietic chimerism 50 days after cancer cell inoculation and all showed 25-50% huCD45$^+$ cells in the PBL, indicating successful engraftment (FIG. 3). The results showed that timing of cancer cell line engraftment has no significant (if any) effect on CD45$^+$ cell population, in the non-HLA matched humanized NSG PDX model.

Example 5 Humanization has No Significant Impact on PDX Growth Kinetics

An important question not addressed by these above experiments was whether the presence of human immune cells influenced tumor growth rates when compared to their growth rates in normal, non-humanized NSG mice.

To determine whether humanization in the NSG mouse model has any significant impact on growth kinetics of non-HLA matched PDX, three fresh PDX tumor samples, breast cancer BR0744 (FIG. 4A), lung cancer LG0977 (FIG. 4B), and soft tissue sarcoma SA0209 (FIG. 4C), were independently engrafted in parallel into either the NSG mouse model, or the huCD34-humanized NSG mouse model, using substantially the same methods as described above, and the PDX growth curves were measured and plotted accordingly.

Figure 4A:
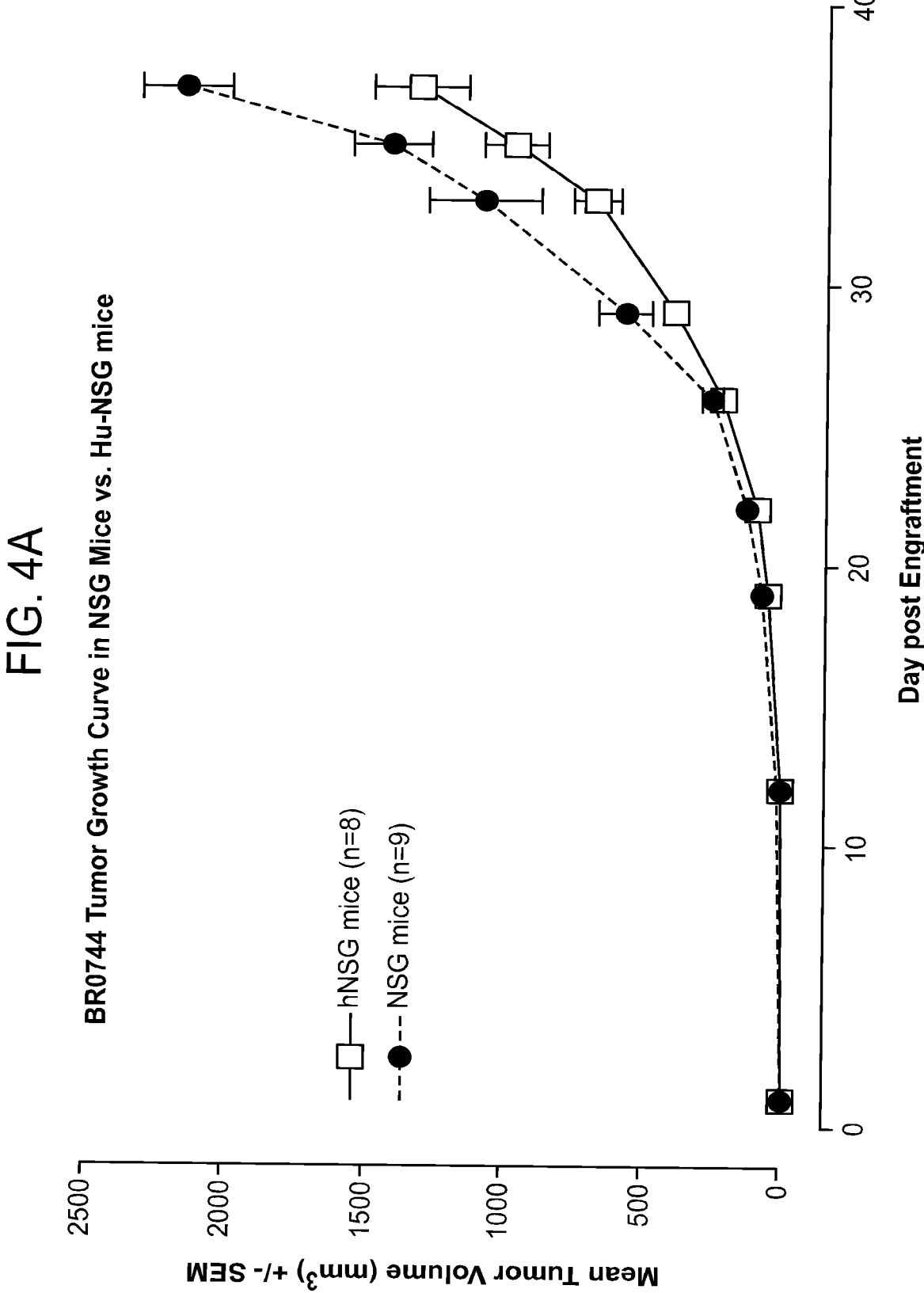
Figure 4B:
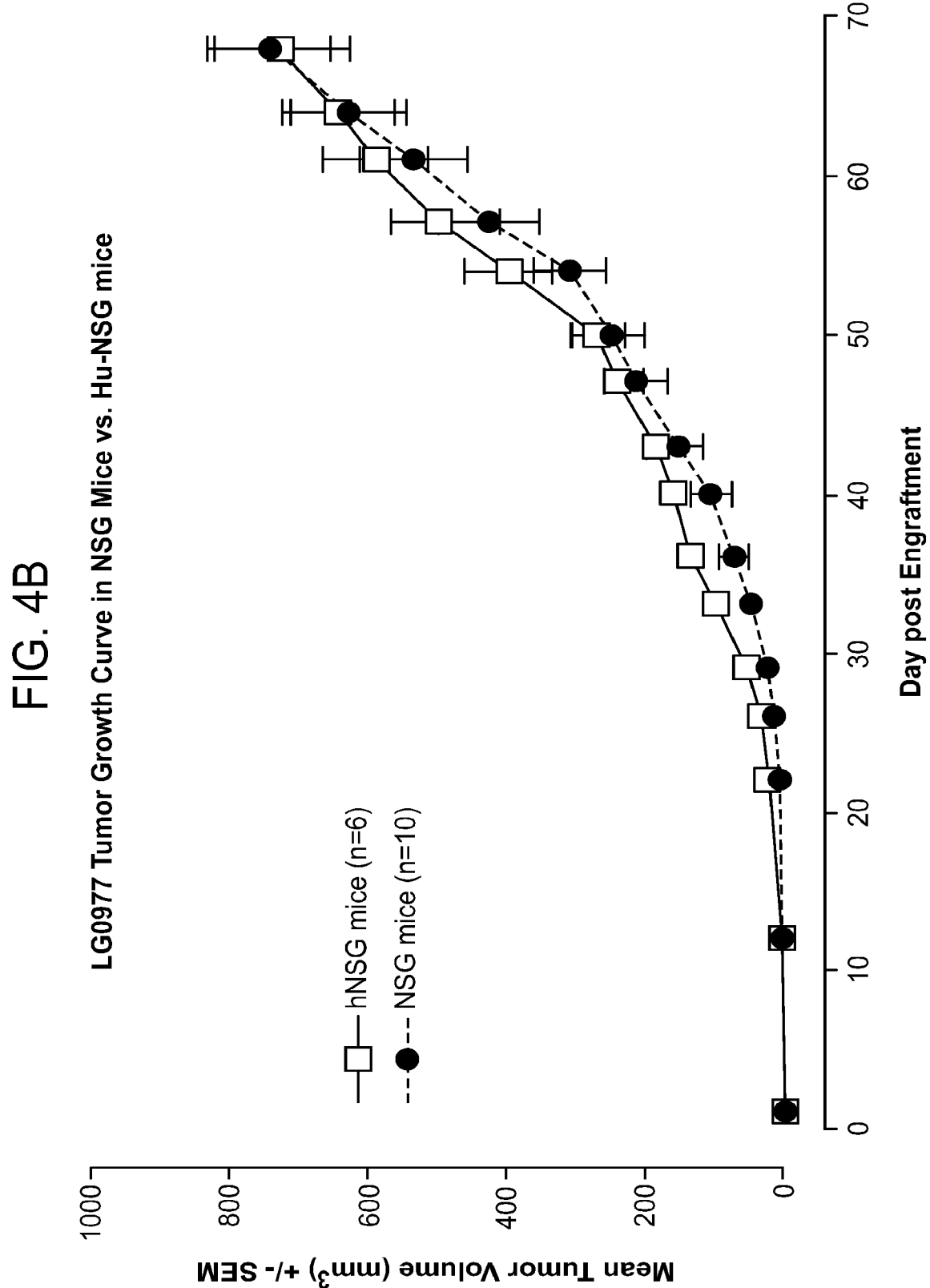
Figure 4C:
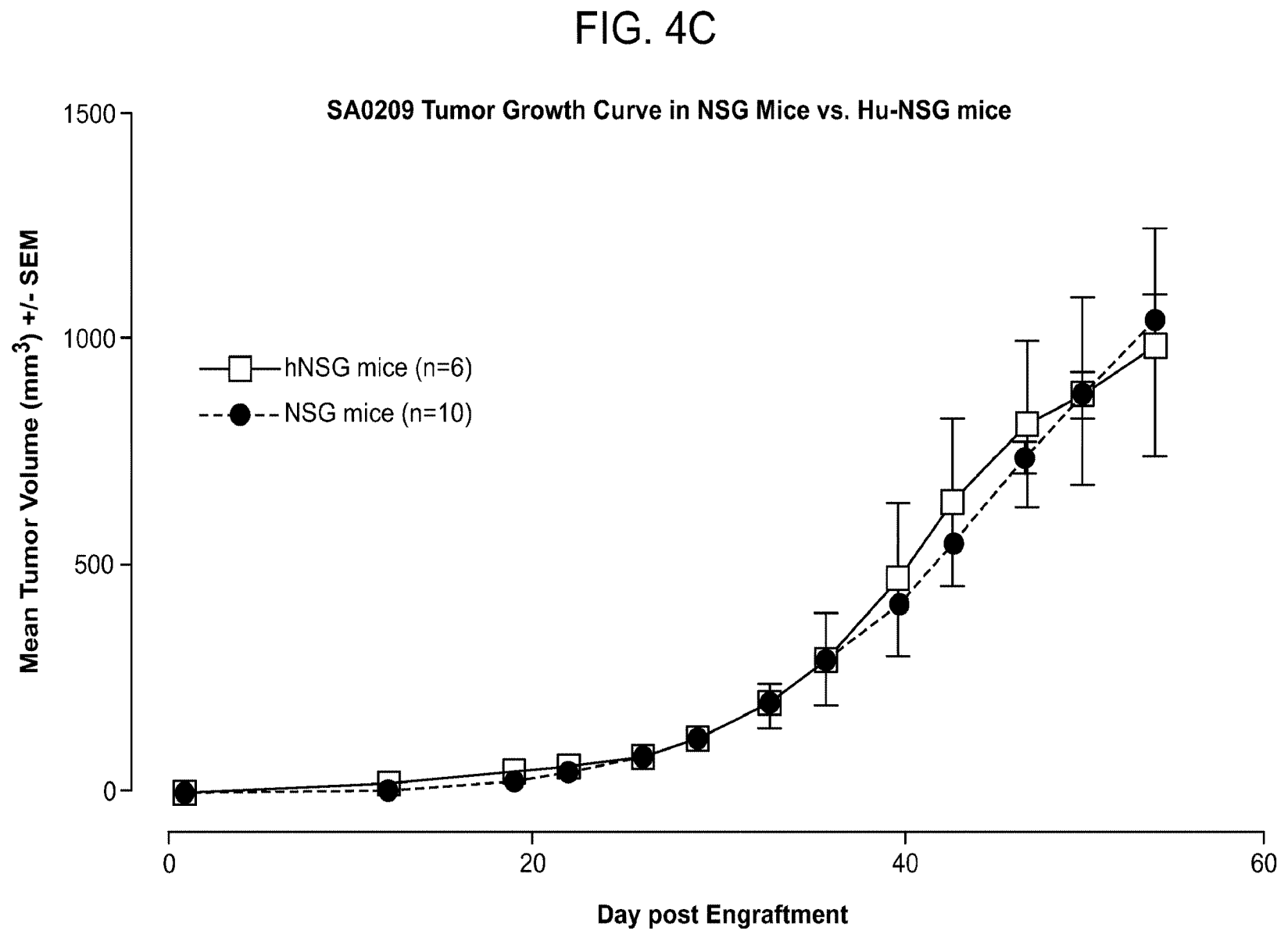

In both the NSG and humanized NSG models, take rate for all three tumors were 100%, and tumors developed in each of the engrafted hosts. Only the breast tumor grew at a slightly faster rate in NSG versus hu-CD34 NSG recipients (FIG. 4A); the other two tumors grew at the same rate in both hosts (FIGS. 4B and 4C). But overall, there is no significant difference in tumor growth curves in NSG vs. hNSG models in the PDX tumors over the entire 40-70-day post engraftment experimental period.

Figures 5A, 5B, 5C:
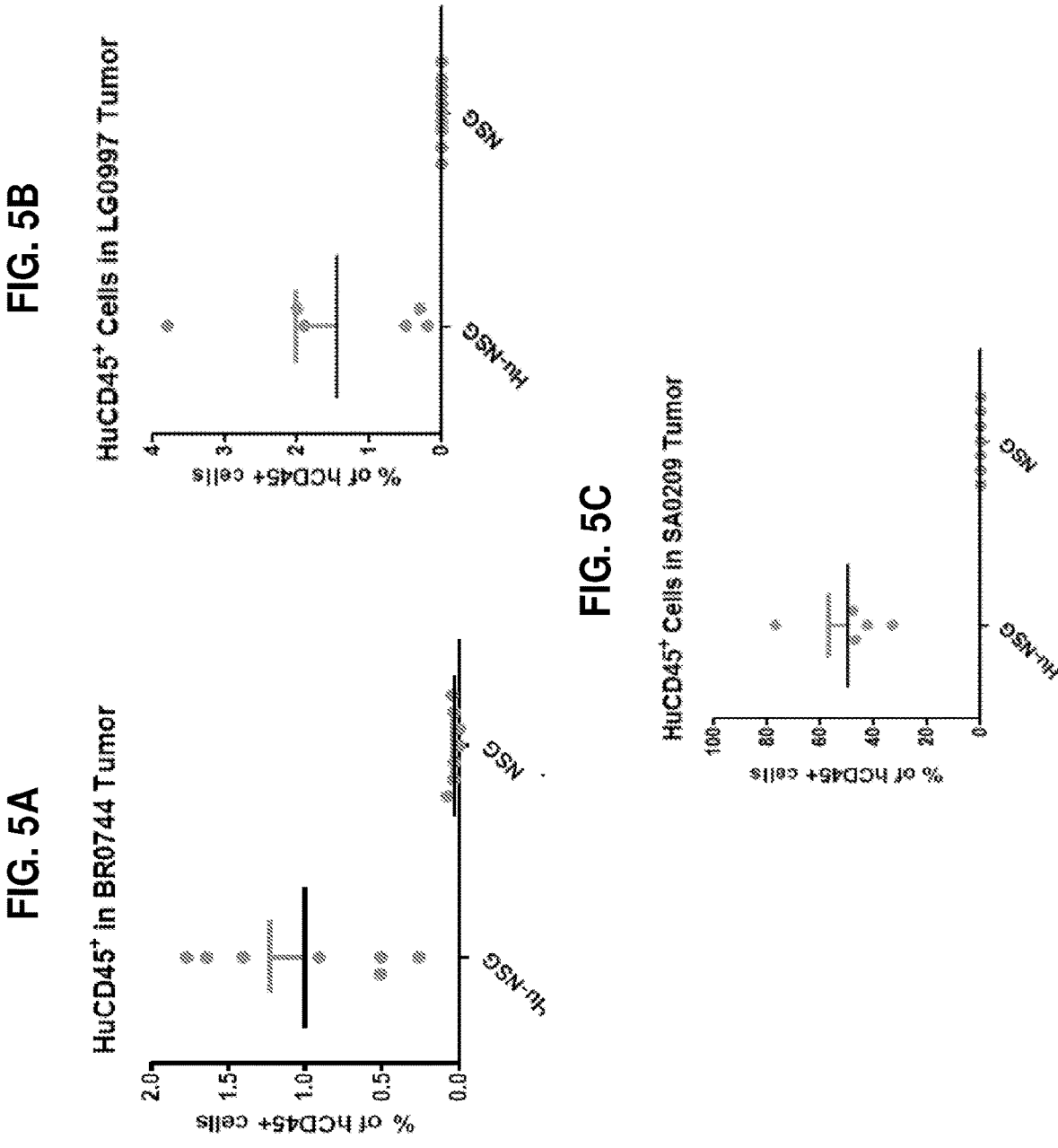
FIGS. 5A-5C show percentage of hCD45$^+$ cells over total tumor (BR0744, LG0977, and SA0209, respectively) population in NSG vs humanized NSG models.

In all hNSG experimental groups, hCD45$^+$ cells in peripheral blood were above 20%, suggesting that the humanization was successful. Also see FIG. 5A-5C, showing that no hCD45$^+$ cells were observed in the non-humanized NSG mice.

At the end of the tumor growth study, tumors were also collected and analyzed by flow cytometry for the presence of TILs. All three tumors contained human CD4$^+$ and CD8$^+$ T-cells, but few CD19$^+$ B cells were detected (See FIGS. 6A-6C). While not wishing to be bound by any particular theory, the failure of the TILs to slow tumor growth in the hu-CD34 NSG recipients suggests that T-cells that recognized the tumor may have become anergic.

Together, these results demonstrate that hu-CD34 NSG mice support non-HLA matched tumor growth and that the presence of human immune cells does not significantly impact tumor take or growth rates.

Example 6 Hu-CD34 NSG™ PDX Mice are Functional Platform for Evaluating Drug Efficacy The ability of the humanized NSG mice to support the growth of non-HLA matched human tumors, as demonstrated above, was an important finding in the development of this preclinical testing platform.

To test whether the subject Hu-CD34 NSG™ mice with non-HLA matched PDX can be used to evaluate drug efficacy against the PDX, using clinically relevant standard-of-care (SOC) treatments, tumor growth curves over 21 days were obtained for a negative control/vehicle group, and two treatment groups using 5-FU and Avastin, respectively, against the colon cancer CN1572P5 PDX. Specifically, 5-FU was administered i.v. at a dose of about 20 mg/kg body weight, Q7d×2 (every 7 days, 2 total doses). Avastin was administered i.p. at a dose of about 10 mg/kg body weight, twice a week, 5 total doses. Vehicle (D5W) was administered i.v., Q7d×3.

Figure 7A:
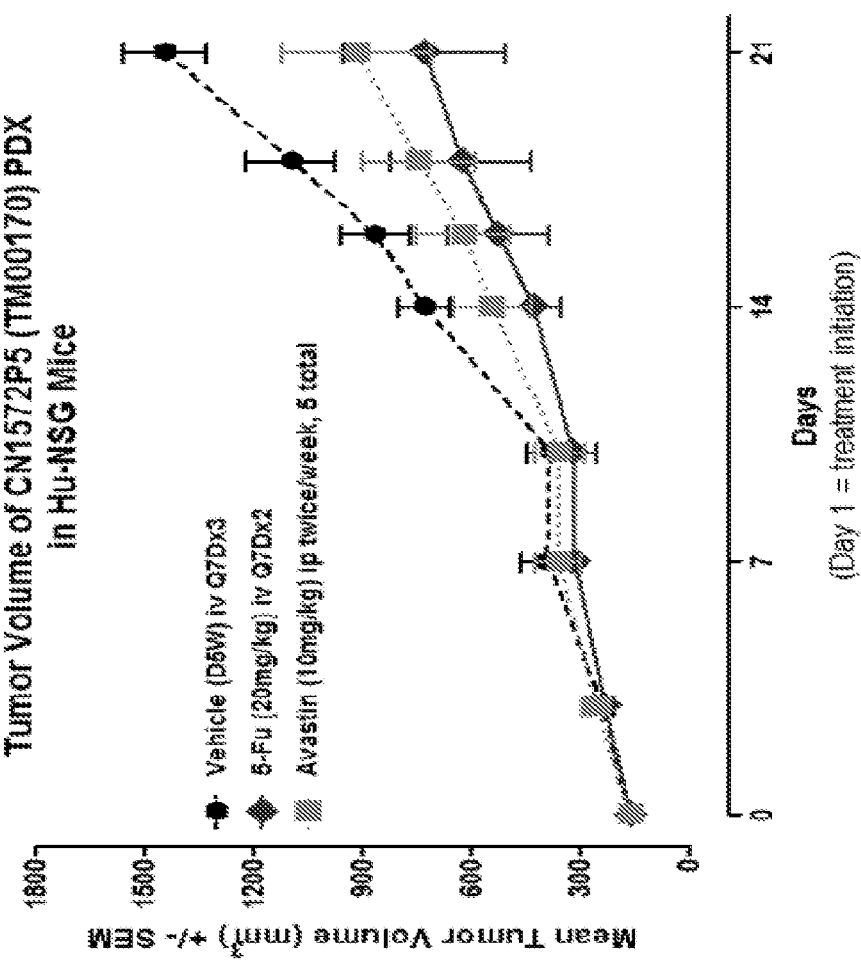
FIG. 7A shows tumor volume curves of the colon cancer CN1572P5 PDX in non-HLA matched humanized NSG model, treated by 5-FU, Avastin, and vehicle control at the indicated dosing regimens.
Figure 7B:
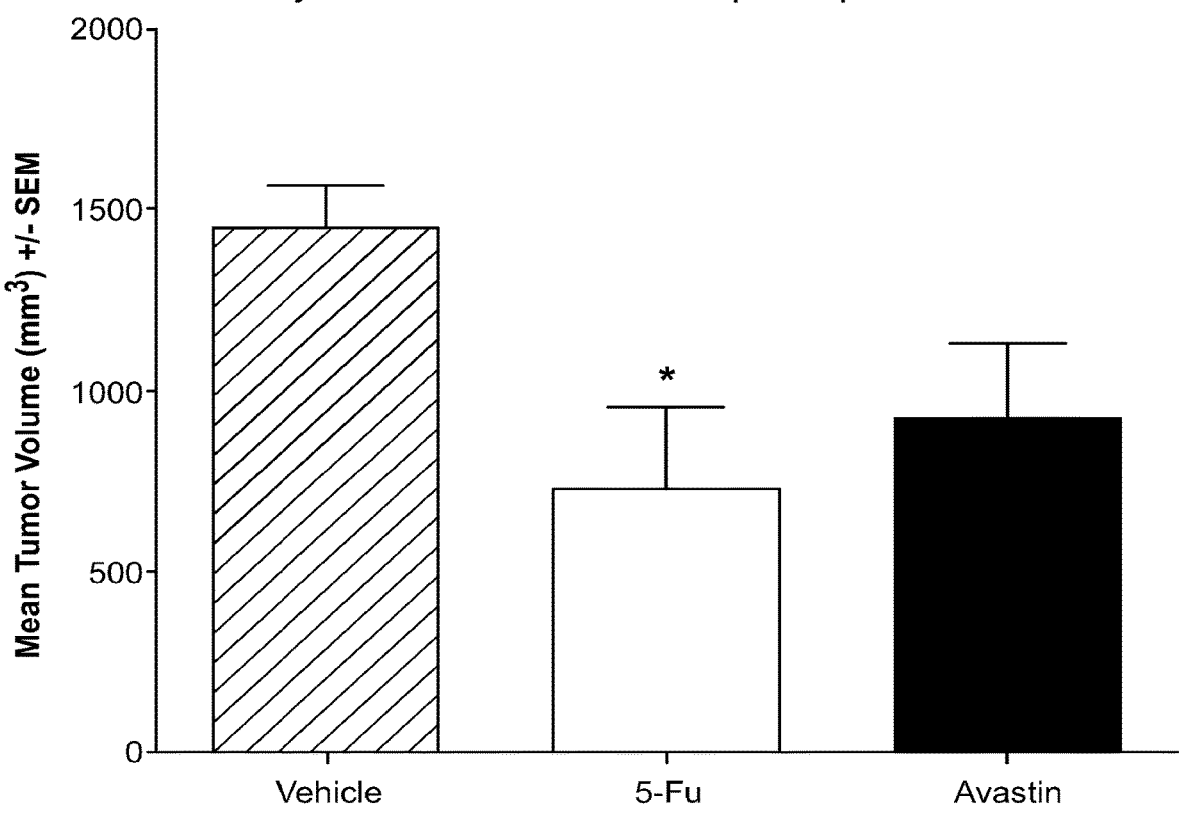
FIG. 7B shows mean tumor volume on Study Day 21 in the three groups.

The results in FIGS. 7A and 7B show that both 5-FU and Avastin are both effective against the non-HLA matched colon cancer PDX in the subject humanized NSG model. This demonstrates that the subject non-HLA matched Hu-CD34 NSG PDX model is a functional platform for evaluating the efficacy of clinically relevant standard-of-care (SOC) drugs.

Example 7 Keytruda and Cisplatin Inhibit the Growth of PD-L1$^+$ MDA-MB-231 Breast Cancer Tumor Model in Hu-CD34 NSG™

Programmed cell death protein 1 (also known as PD-1 and CD279), is a protein that in humans is encoded by the PDCD1 gene. PD-1 is an immunoinhibitory cell surface receptor that belongs to the CD28 family of immunoglobulin (Ig) superfamily, and is expressed on T cells, pro-B cells, monocytes, natural killer cells, and many tumor-infiltrating lymphocytes (TILs). It is an important immune "checkpoint" receptor that inhibits the T-cell response and plays a key role in modulating T-cell function.

PD-1 binds two ligands, PD-L1 and PD-L2, both of which have been found on tumor cells and both of which have been used by tumor cells to engage the PD-1 receptor on activated T cells to suppress the function of the activated T cells, thus evading immune response against tumor cells. Hence, PD-1 and its ligands play an important role in down regulating the immune system by preventing the activation of T-cells, which in turn down-regulates immune response against cancer, but also reduces autoimmunity and promotes self-tolerance. The inhibitory effect of PD-1 is thought to be accomplished through a dual mechanism of promoting apoptosis (programmed cell death) in antigen specific T-cells in lymph nodes, while simultaneously reducing apoptosis in regulatory T cells (suppressor T cells).

A new class of drugs that block PD-1, the PD-1 inhibitors, activate the immune system to attack tumors and are therefore useful to treat cancer. For example, monoclonal antibodies against PD-1 may boost the immune system, thus useful for treatment of cancer. In addition, many tumor cells express the immunosuppressive PD-1 ligand PD-L1. Thus inhibition of the interaction between PD-1 and PD-L1 can enhance T-cell responses in vitro and mediate preclinical antitumor activity.

One such anti-PD-1 antibody drug, nivolumab, (Opdivo—Bristol Myers Squibb), produced complete or partial responses in non-small-cell lung cancer, melanoma, and renal-cell cancer, in a clinical trial with a total of 296 patients. Nivolumab also targets PD-1 receptors, and was approved in Japan in July 2014 and by the US FDA in December 2014 to treat metastatic melanoma.

Another such anti-PD-1 antibody drug, pembrolizumab (Keytruda, MK-3475, Merck), targets PD-1 receptors, and was approved by the FDA in September 2014 to treat metastatic melanoma. Pembrolizumab has been made accessible to advanced melanoma patients in the UK via UK Early Access to Medicines Scheme (EAMS) in March 2015. It is also being used in clinical trials in the US for lung cancer and mesothelioma.

Other drugs in early stage development targeting PD-1 receptors include Pidilizumab (CT-011, Cure Tech), BMS 936559 (Bristol Myers Squibb), and MPDL328OA (Roche).

On the other hand, cisplatin is the first member of now a class of platinum-containing anti-cancer chemotherapy drugs, which also includes carboplatin and oxaliplatin. These platinum complexes react in vivo, binding to and causing crosslinking of DNA, which ultimately triggers apoptosis (programmed cell death).

To determine if engrafted PDX tumors would also respond to clinically relevant immuno-oncology checkpoint inhibitors, or if such checkpoint inhibitors could reactivate anti-tumor responses in the resident human immune cells, a series of experiments were designed and conducted to address these questions.

First, to determine if the checkpoint inhibitor pembrolizumab (Keytruda) is efficacious in the subject non-HLA matched PDX humanized NSG model, a PDX huNSG model was established according to the methods of the invention. Specifically, humanized NSG mice (human CD45$^+$ cells were found to be more than 25% in the peripheral blood of the hNSG mice, demonstrating successful huCD34 engraftment) were engrafted with 5×10$^6$ of non-HLA matched PD-L1-positive breast cancer cell line MDA-MB-231 cells per mouse, via s.c. inoculation with matrigel. This cell line expresses very high levels of PD-L1 on the tumor cell surface that can bind to PD-1 on T-cells and induce anergy—about 94.3% of the MDA-MB-231 cells expressed PD-L1. The tumor-engrafted humanized NSG mice were then treated either with vehicle, Cisplatin, or Prembrolizumab (Keytruda).

Tumor growth curves over 21 days were obtained for a negative control/vehicle group, and two treatment groups using cisplatin and pembrolizumab (Keytruda), respectively, against the MDA-MB-231 PDX. Specifically, cisplatin was administered i.v. at a dose of about 2 mg/kg body weight, Q7d×2 (every 7 days, 2 total doses). Pembrolizumab (Keytruda) was administered i.p. at a dose of about 5-10 mg/kg body weight, Q5d×4 (every 5 days, 4 total doses). Vehicle (Saline) was administered i.p., Q5d×4.

Figure 8A:
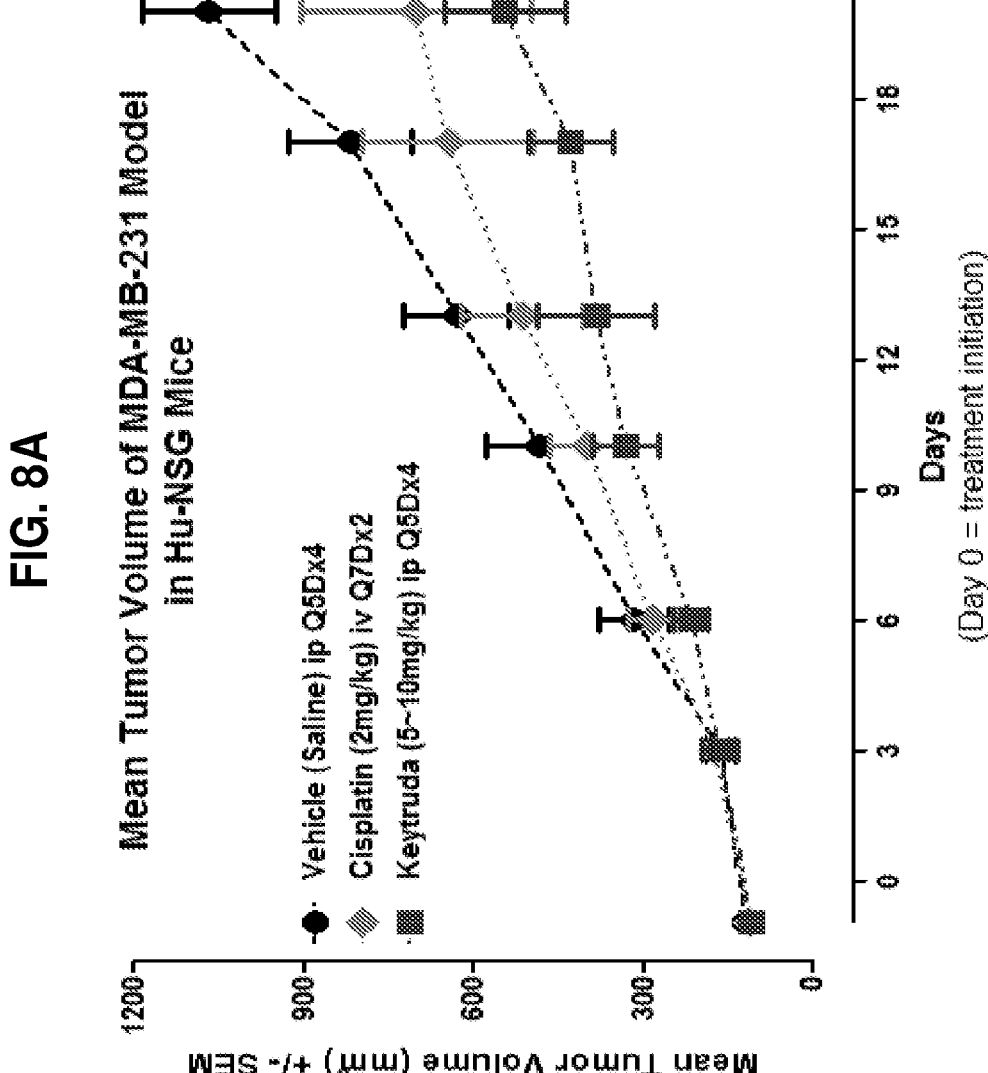
FIG. 8A shows tumor volume curves of the breast cancer MDA-MB-231 PDX in non-HLA matched humanized NSG model, treated by cisplatin, pembrolizumab (Keytruda), and vehicle control at the indicated dosing regimens.
Figure 8B:
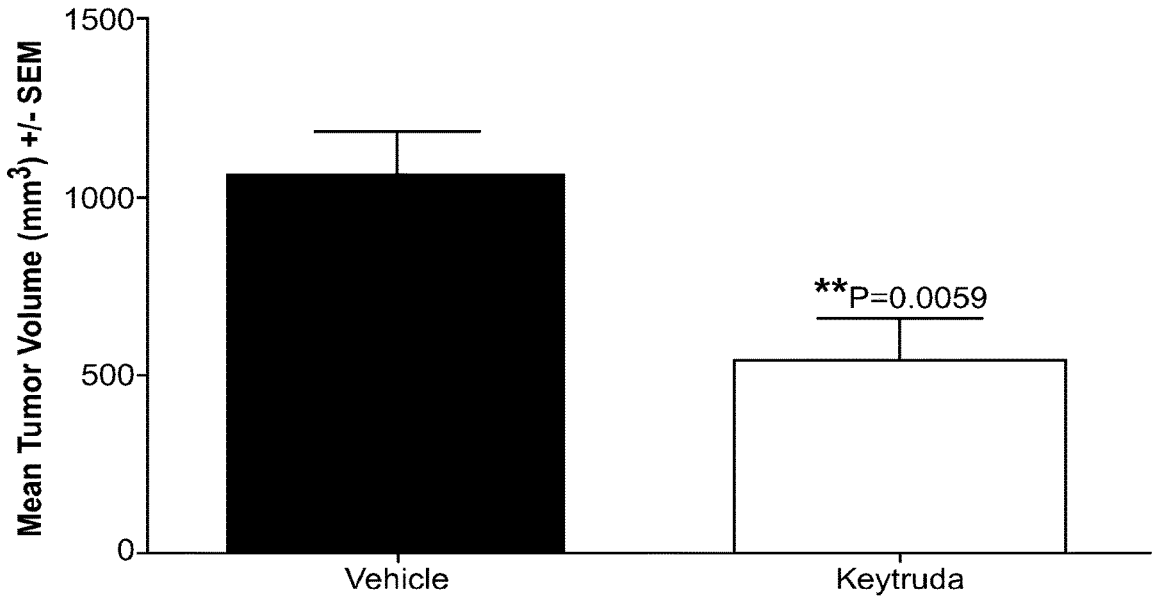
FIG. 8B shows mean tumor volume on Study Day 20 in the pembrolizumab (Keytruda) and vehicle groups. A similar experiment as the one in FIG. 8A was run and the result was shown in FIG. 8C.
Figure 8C:
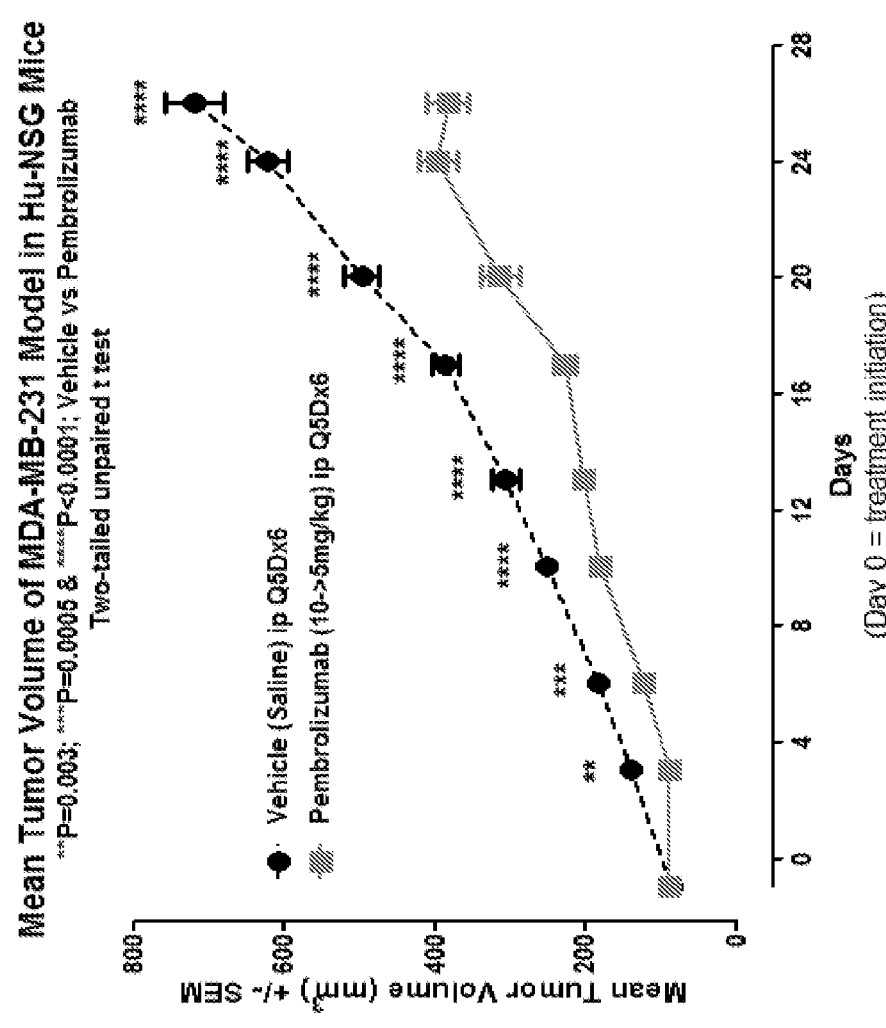
Figures 9A, 9B, 9C, 9D:
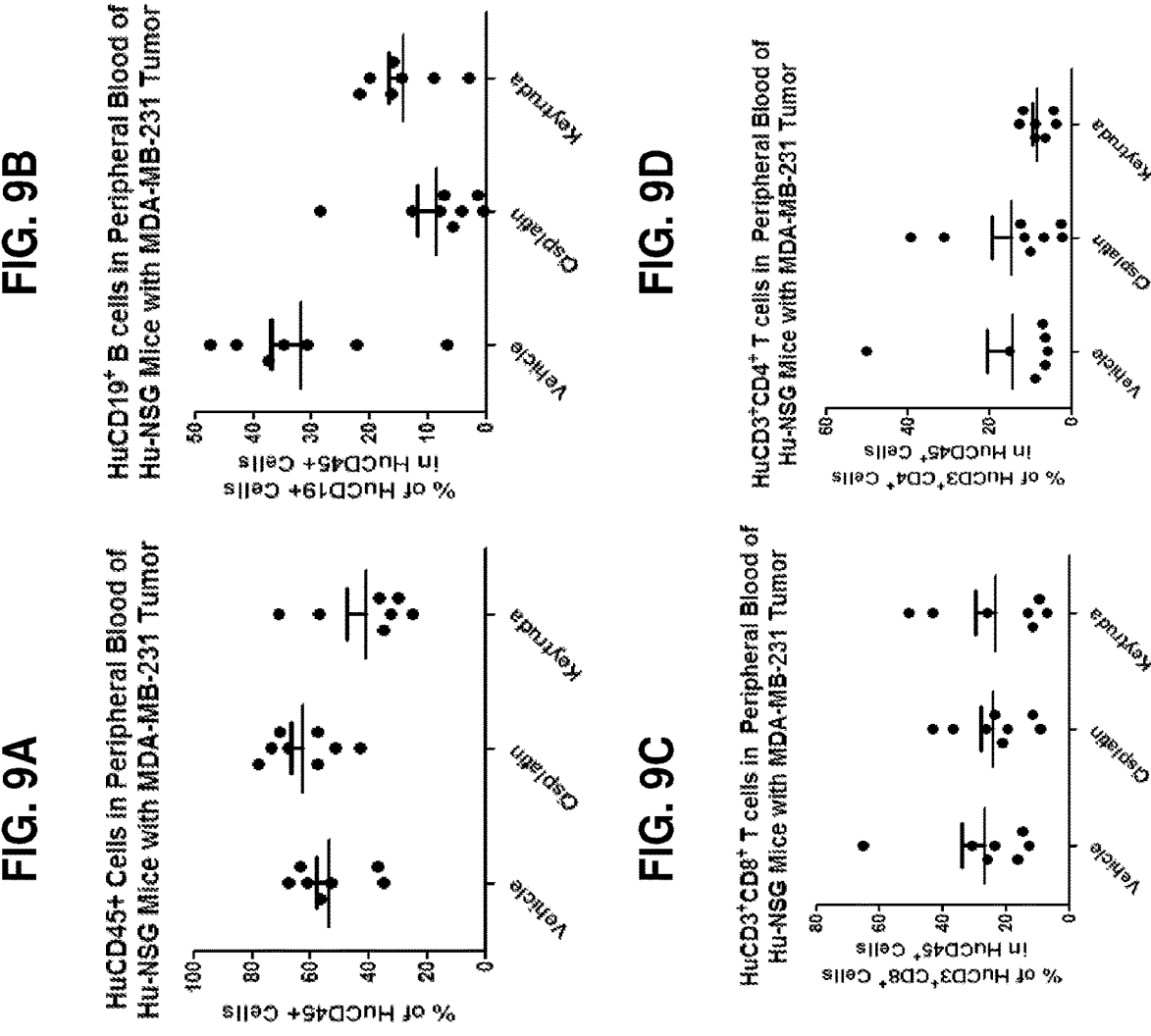
FIGS. 9A-9D show that human T cells (both CD3$^+$CD4$^+$ and CD3$^+$CD8$^+$) and B cells (CD19$^+$) are present in the peripheral blood of the subject Hu-CD34 NSG™ non-HLA matched MDA-MB-231 PDX mice.

Cisplatin is a platinum-containing chemotherapeutic that causes DNA cross-linking and apoptosis in rapidly dividing cells. Cisplatin treatment only marginally reduced the growth rate of the MDA-MB-231 tumors in the humanized mice. In contrast, Keytruda delayed tumor growth significantly within ~2 weeks after treatment was started (FIGS. 8A and 8B).

At the termination of the growth study, peripheral blood of the experimental mice were collected and assayed for human CD19$^+$ B cells and human CD4$^+$ and CD8$^+$ T-cells. FIGS. 9A-9D show that human T cells, including both CD3$^+$CD4$^+$ and CD3$^+$CD8$^+$ T cells, and CD19$^+$ B cells, are present in the peripheral blood of the subject Hu-CD34 NSG™ non-HLA matched MDA-MB-231 PDX mice.

Tumors were also collected and assayed for human CD4$^+$ and CD8$^+$ infiltrating T-cells. FIG. 10A-10C show that human T cells (both CD3$^+$CD4$^+$ and CD3$^+$CD8$^+$ T cells) are present in the tumor tissue of the subject Hu-CD34 NSG™ non-HLA matched MDA-MB-231 PDX mice.

Thus all three treatment groups showed similar percentages of these cells irrespective of treatment. The absence of additional TILs in the Keytruda-treated tumors suggests that the slower tumor growth resulted from re-activation of resident TILs and not from additional stimulation of TIL infiltration from PBL or spleen.

The data again demonstrates that the subject non-HLA matched Hu-CD34 NSG PDX model is a functional platform for evaluating drug efficacy, including immunomodulatory drugs that may rely on the function of the engrafted human immune cells.

Example 8 Keytruda and Cisplatin Inhibit the Growth of PD-L1$^+$ TNBC BR1126 Breast Cancer Tumor Model in Hu-CD34 NSG™

Substantially the same result as in Example 7 was obtained in this example, where the non-HLA matched PD-L1-positive breast cancer cell line MDA-MB-231 cells were replaced with the non-HLA matched PD-L1-positive breast cancer cell line BR1126 cells—a triple negative breast cancer (TNBC) cell line. Triple negative breast cancer is an aggressive subset of breast cancer with limited treatment options. PD-L1 expression has been reported in patients with TNBC. When PD-L1 expression was evaluated in TILs, it correlated with higher grade and larger-sized tumors. Tumor PD-L1 expression also correlates with the infiltration of T-regulatory cells in TNBC, findings that suggest the role of PD-L1-expressing tumors and the PD-1/PD-L1-expressing TILs in regulating immune response in TNBC.

Specifically, humanized NSG mice were engrafted with 5×10$^6$ of non-HLA matched PD-L1-positive breast cancer cell line BR1126 cells per mouse via s.c. inoculation. This can be done with the presence of matrigel. About 56.9% of the BR1126 cells expressed PD-L1. Human CD45$^+$ cells were found to be more than 25% in the peripheral blood of the hNSG mice.

Tumor growth curves over 21 days were obtained for a negative control/vehicle group, and two treatment groups using cisplatin and pembrolizumab (Keytruda), respectively, against the BR1126 PDX. Specifically, cisplatin was administered i.v. at a dose of about 2 mg/kg body weight, Q7d×3 (every 7 days, 3 total doses). Pembrolizumab (Keytruda) was administered i.p. at a dose of about 5-10 mg/kg body weight, Q5d×4 (every 5 days, 4 total doses). Vehicle (Saline) was administered i.p., Q5d×4.

Figure 11A:
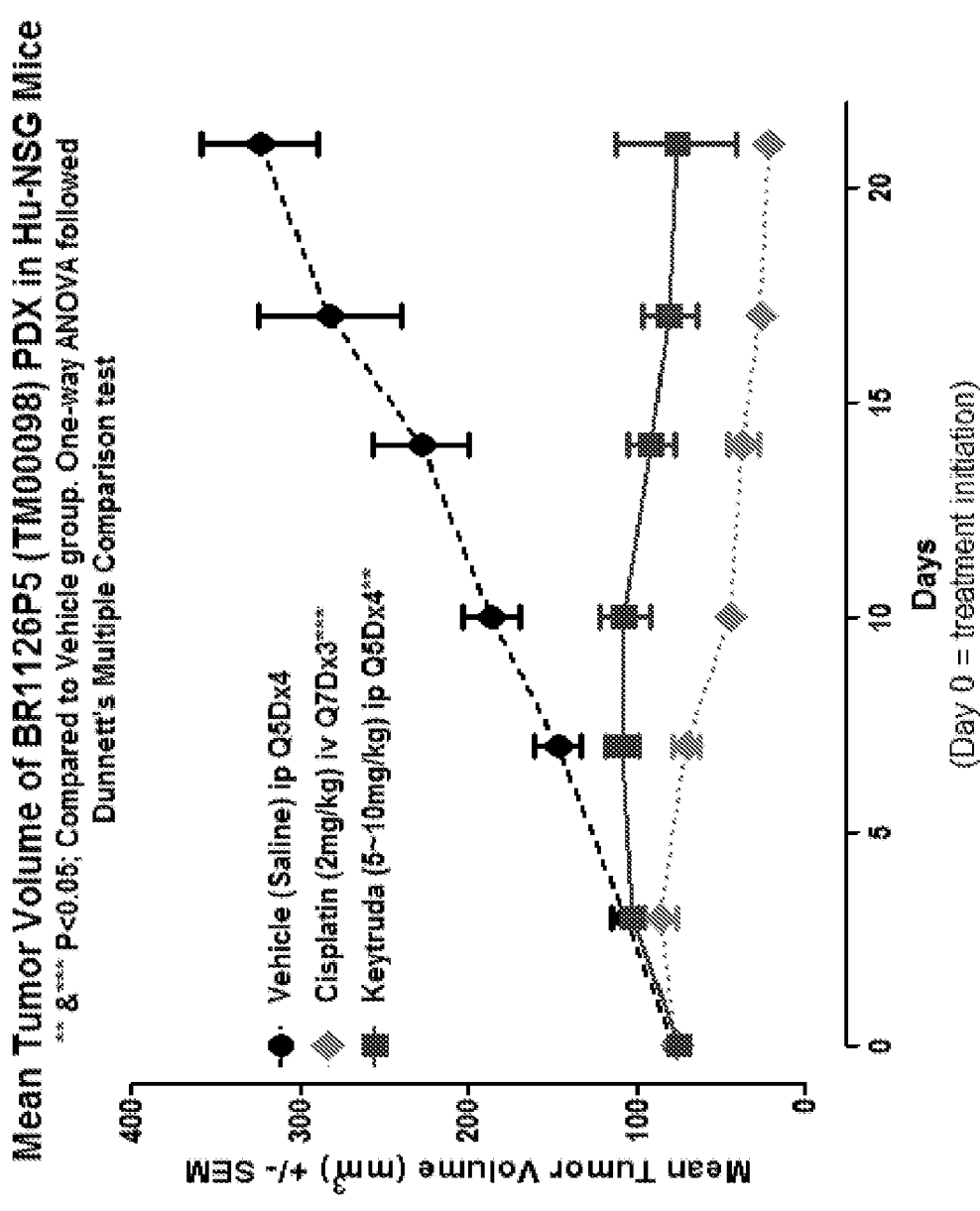
FIG. 11A shows tumor volume curves of the breast cancer BR1126 PDX in non-HLA matched humanized NSG model, treated by cisplatin, pembrolizumab (Keytruda), and vehicle control at the indicated dosing regimens.
Figure 11B:
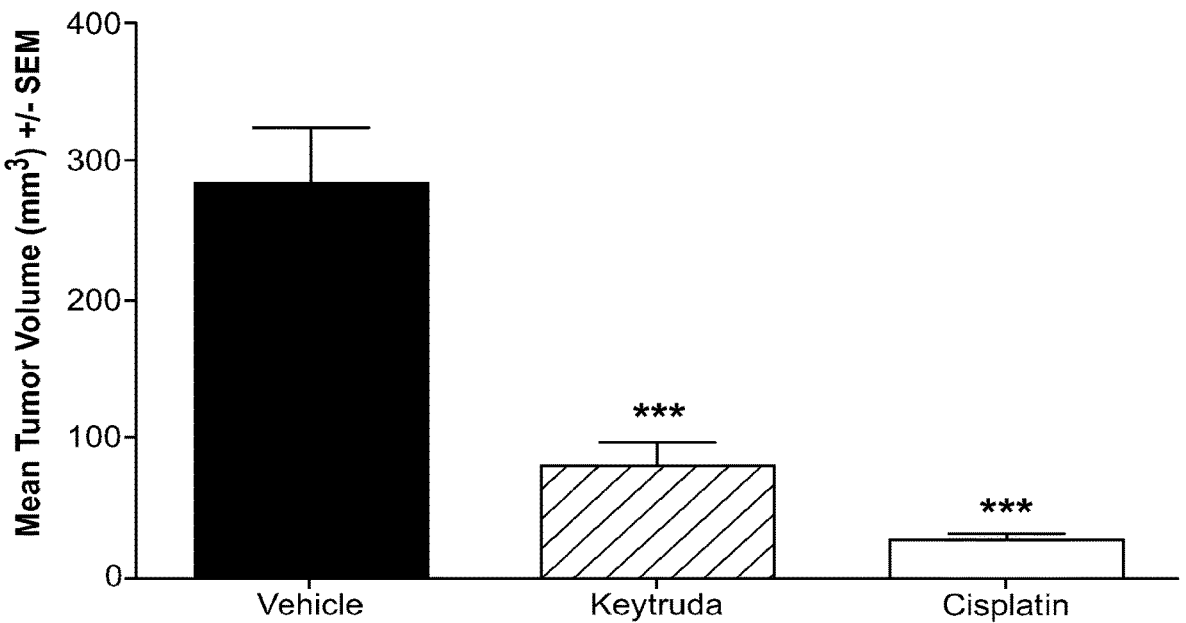
FIG. 11B shows mean tumor volume on Study Day 17 in the three groups. A similar experiment as the one in FIG. 11A was run and the result was shown in FIG. 11C.
Figure 11C:
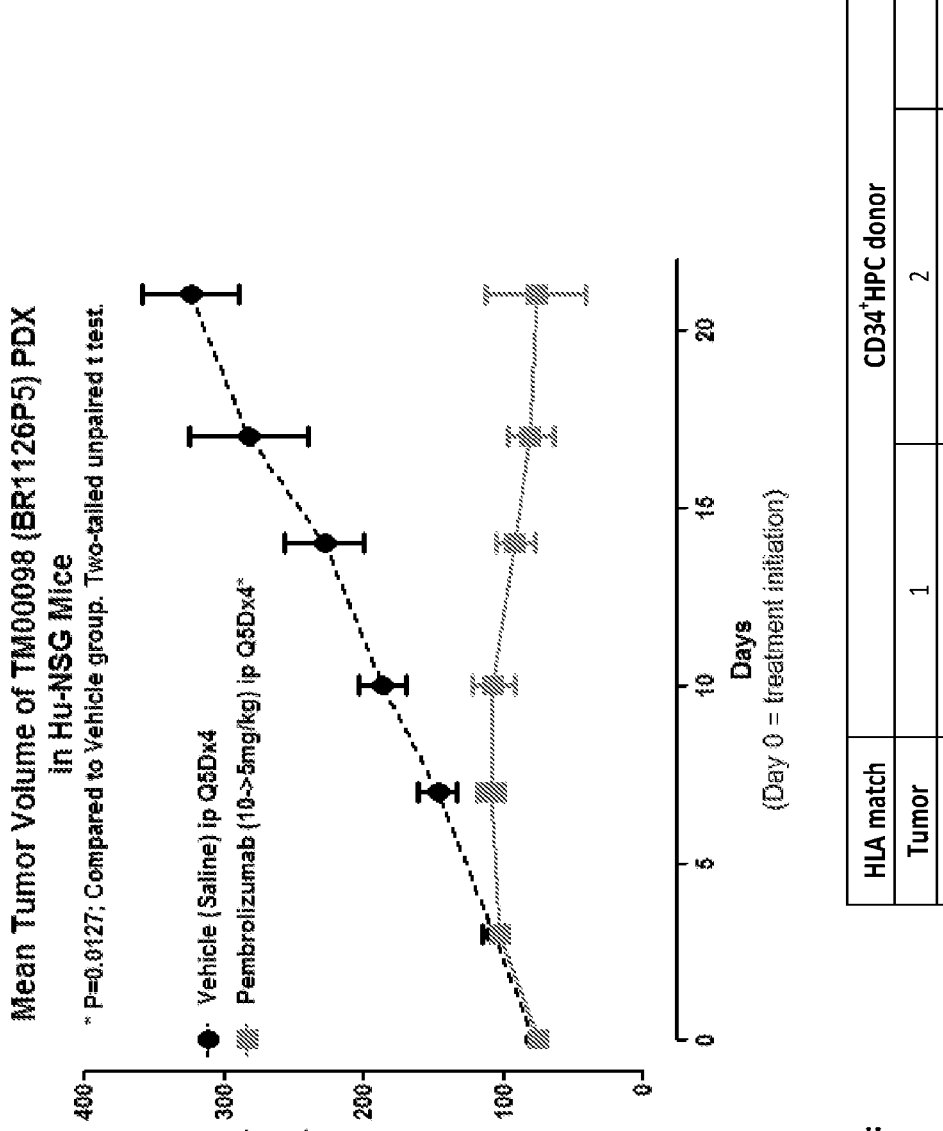
Figures 12A, 12B, 12C, 12D:
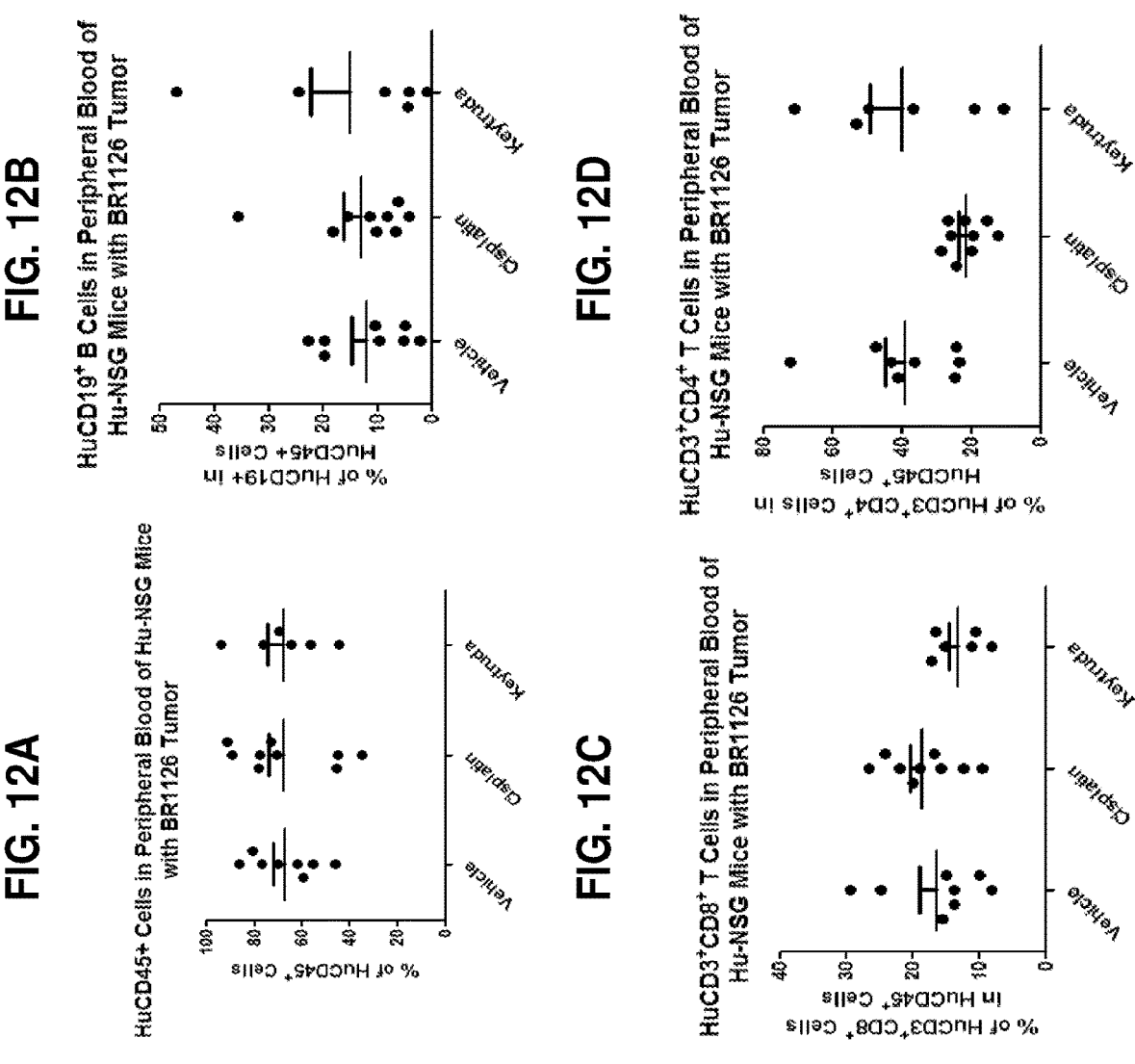
FIGS. 12A-12D show that human T cells (both CD3$^+$CD4$^+$ and CD3$^+$CD8$^+$) and B cells (CD19$^+$) are present in the peripheral blood of the subject Hu-CD34 NSG™ non-HLA matched BR1126 PDX mice.
Figures 13A, 13B, 13C, 13D:
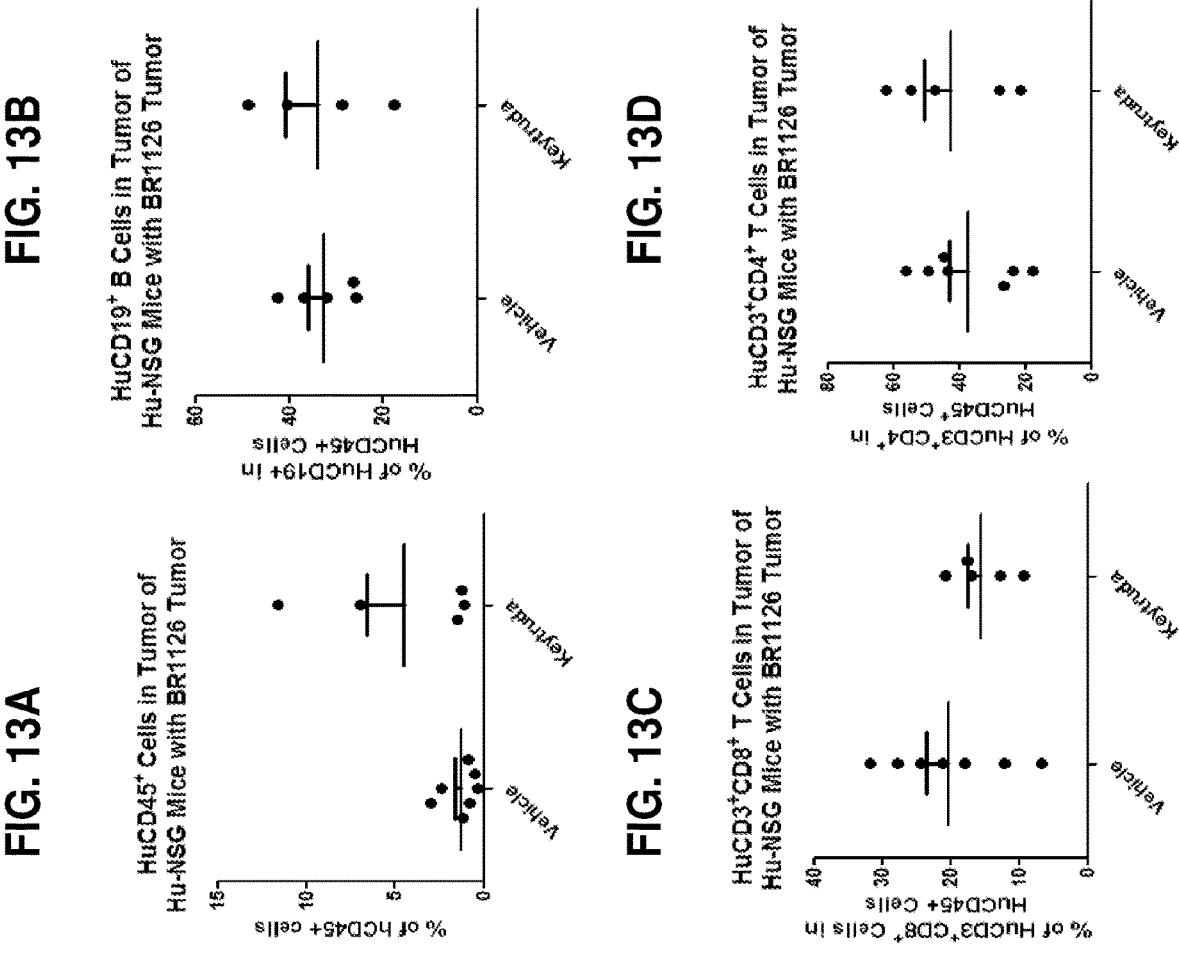
FIG. 13A-13D show that human T and B cells are present in the tumor tissue of the subject Hu-CD34 NSG™ non-HLA matched BR1126 PDX mice.
Figures 13E, 13F, 13G, 13H:
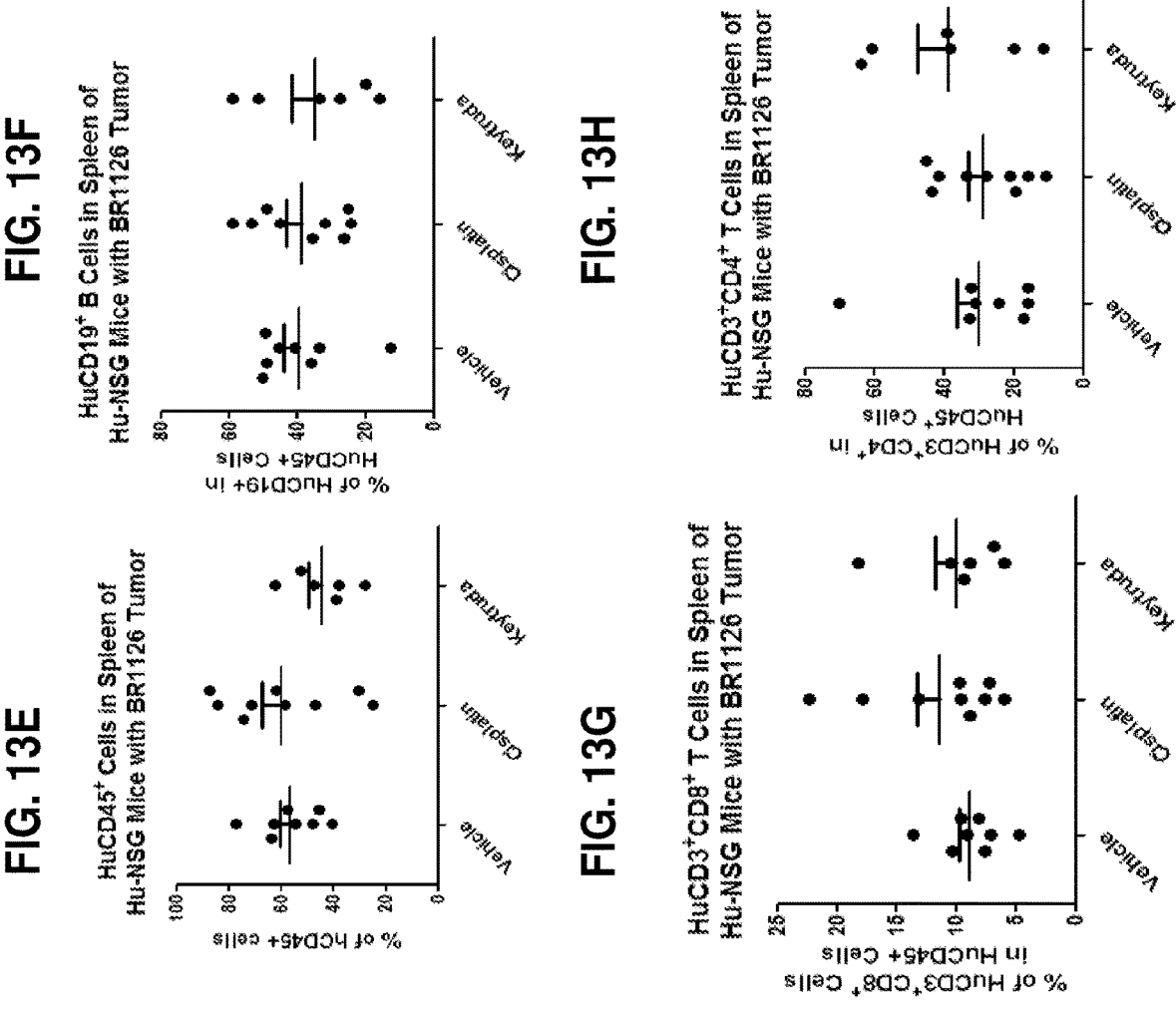
FIG. 13E-13H show that human T and B cells are present in the spleens of the subject Hu-CD34 NSG™ non-HLA matched BR1126 PDX mice.

The results in FIGS. 11A and 11B show that both Cisplatin and Keytruda significantly reduced tumor growth compared to the vehicle control, against the non-HLA matched PD-L1$^+$ breast cancer PDX in the subject humanized NSG model.

FIGS. 12A-12D further show that human T cells, including both CD3$^+$CD4$^+$ and CD3$^+$CD8$^+$ T cells, and CD19$^+$ B cells, are present in the peripheral blood of the subject Hu-CD34 NSG™ non-HLA matched BR1126 PDX mice.

Tumors from the Keytruda-treated mice were collected at the end of the study and examined for lymphocyte infiltration. FIG. 13A-13D show that human T cells (both CD3$^+$CD4$^+$ and CD3$^+$CD8$^+$ T cells) and CD19$^+$ B cells are present in the tumor tissue of the subject Hu-CD34 NSG™ non-HLA matched BR1126 PDX mice. Thus, as in the cancer cell line experiment, the tumors were also infiltrated with human CD4$^+$ and CD8$^+$ T-cells, as well as with human B cells, and treatment with Keytruda did not increase tumor infiltration compared to the vehicle treated mice, suggesting again that the slower tumor growth resulted from re-activation of resident immune effector cells.

FIG. 13E-13H further show that human T cells (both CD3$^+$CD4$^+$ and CD3$^+$CD8$^+$ T cells) and CD19$^+$ B cells are present in the spleens of the subject Hu-CD34 NSG™ non-HLA matched BR1126 PDX mice.

In a similar experiment, immuno-staining was conducted on PDX tumor samples treated by chemotherapy alone, anti-PD1 agent Keytruda, and anti-CTLA4 agent ipilimumab, for the presence of CD45$^+$CD8$^+$ infiltrating T lymphocytes. FIG. 16 shows that treatments using the anti-PD1 agent Keytruda, and the anti-CTLA4 agent ipilimumab, led to strong presence of the infiltrating CD45$^+$CD8$^+$ T lymphocytes, compared to chemotherapy alone.

This again demonstrates that the subject non-HLA matched Hu-CD34 NSG PDX model is a functional platform for evaluating drug efficacy, including immunomodulatory drugs that may rely on the function of the engrafted human immune cells.

Example 9 Keytruda+/− Docetaxol Inhibit the Growth of PD-L1$^+$ LG1306 Lung Cancer Tumor Model in Hu-CD34 NSG™

The experiment was conducted to determine if combinatorial treatment of a tumor in hu-CD34 NSG mice would show greater efficacy than either single agent therapy.

Substantially the same result as in Examples 7 and 8 was obtained in this example, where the non-HLA matched PD-L1-positive breast cancer cell line MDA-MB-231 cells or BR1126 cells were replaced with the non-HLA matched PD-L1-positive lung cancer cell line LG1306.

Specifically, humanized NSG mice were engrafted with 5×10$^6$ of non-HLA matched PD-L1-positive PDX lung cancer cell line LG1306 per mouse. About 89.1% of the LG1306 cells expressed PD-L1. Human CD45$^+$ cells were found to be more than 20% in the peripheral blood of the hNSG mice.

Tumor growth curves over 24 days were obtained for a negative control/vehicle group, and two treatment groups using pembrolizumab (Keytruda), with or without the anti-mitotic chemotherapeutic agent Decotaxol, against the LG1306 PDX. Specifically, Decetaxol, when present, was administered i.v. at a dose of about 10 mg/kg body weight, Q7d×4 (every 7 days, 4 total doses). Pembrolizumab (Keytruda) was administered i.p. at a dose of about 5 mg/kg body weight, Q5d×6 (every 5 days, 6 total doses). Vehicle (Saline) was administered i.p., Q5d×6.

Tumors from mice treated with Keytruda alone showed reduced growth compared to those from vehicle-treated controls, but their responses were highly variable due to one of 10 mice not responding to Keytruda. When Keytruda was combined with Docetaxel, tumor growth was significantly suppressed within 10 days following treatment, with very little mouse-to-mouse (tumor-to-tumor) variability. When the one mouse that did not respond to Keytruda was taken out of the calculations, however, there was no difference between the Keytruda and the combination arms. Both arms showed significant decrease in tumor growth and no additive effects were observed when combining Keytruda and Docetaxel.

Figure 14A:
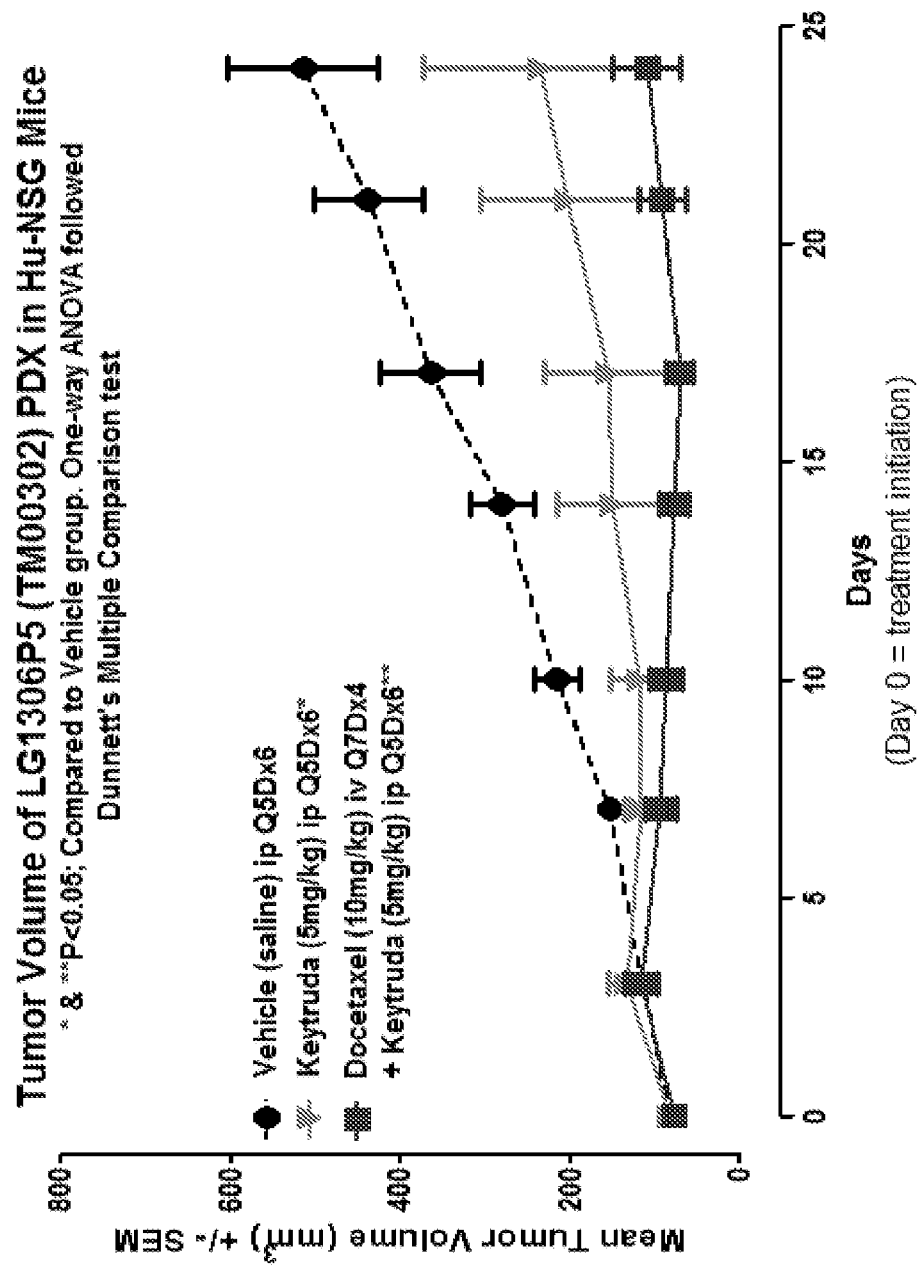
FIG. 14A shows tumor volume curves of the lung cancer LG1306 PDX in non-HLA matched humanized NSG model, treated by pembrolizumab (Keytruda), with or without Decetaxol, and vehicle control at the indicated dosing regimens.
Figure 14B:
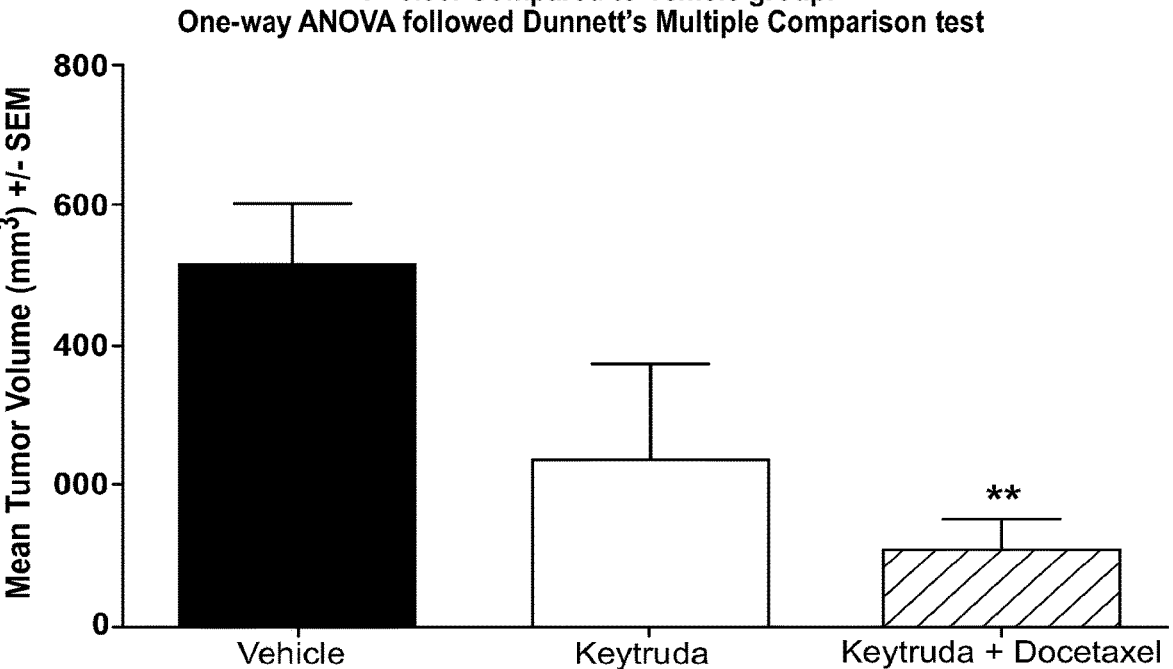
Figure 14C:
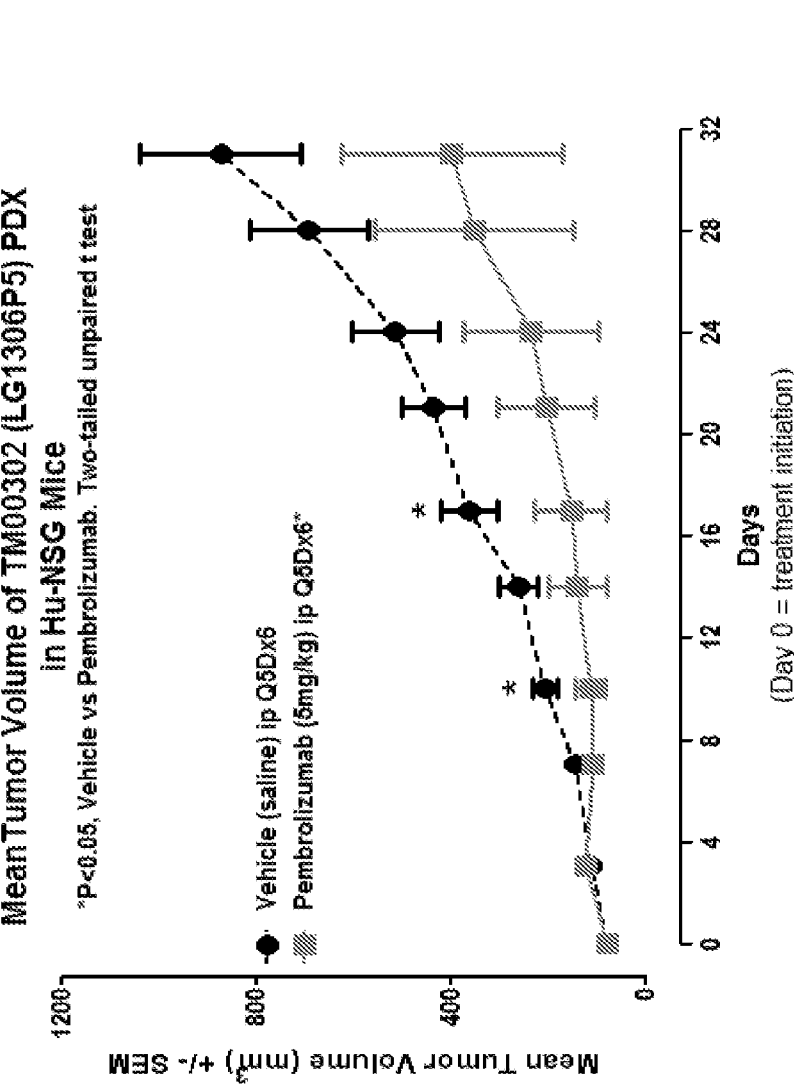

Thus, the results as shown in FIGS. 14A and 14B, showed that pembrolizumab (Keytruda), with or without Decetaxol, are effective against the non-HLA matched PD-L1$^+$ breast cancer PDX in the subject humanized NSG model.

Together, the experiments described herein, particularly the experiments in Examples 6-9 demonstrated that human tumors engrafted in hu-CD34 NSG mice are able to respond to standard-of-care chemotherapeutics. An even more significant finding, however, is that the engrafted tumors appear to evade human immunity much as they do in the patients from which they were derived. Moreover, treatment with a TIL check-point inhibitor presumably releases T-cells from anergy and stimulates their cytotoxicity towards the tumor.

The data demonstrate the hu-CD34 NSG mice as a powerful platform for gathering new insights into the interactions of human immune cells and tumors, and for testing immuno-oncology and combination therapies.

Overall, the results demonstrated in the examples herein demonstrates the engraftment and growth of PDX tumors in the subject humanized mice (e.g., NSG mice), the responses of the engrafted mice to standard-of-care (SOC) treatments, and immune-mediated tumor regression following treatment with a check-point inhibitor. These results support the use of the subject humanized mice (e.g., NSG mice) as a new preclinical bridge for immuno-oncology therapies.

All references, including patent literature, as cited herein are incorporated by reference.

The invention claimed is:

1. A method of producing a mouse model for in vivo preclinical testing, the method comprising:
   (a) introducing CD34$^+$ human hematopoietic stem cells (HSCs) into an immunodeficient non-obese diabetic mouse comprising a homozygous scid mutation and an IL-2 receptor gamma chain deficiency to produce a humanized mouse in which the percentage of human CD45$^+$ cells in peripheral blood is about 20-30%; and
   (b) introducing into the humanized mouse a human PDX about 9, 10, 11, 12, 13, 14, or 15 weeks after introducing the CD34$^+$ human HSCs, wherein the human PDX and the CD34$^+$ human HSCs are non-HLA matched, the human PDX develops into a tumor, and the CD34$^+$ human HSCs mature into human CD19$^+$ B cells and human CD8$^+$ T cells to produce a humanized mouse engrafted with the human tumor.

2. The method of claim 1 further comprising:
   (c) administering an agent to the humanized mouse engrafted with the human tumor.

3. The method of claim 2 further comprising:
   (d) assaying a sample obtained from the humanized mouse of (c) for effectiveness of the agent for treating the tumor.

4. The method of claim 2, wherein the agent is an anti-cancer agent.

5. The method of claim 2, wherein the agent is selected from: small molecules, proteins, peptides, nucleic acids, carbohydrates, oligosaccharides, lipids, and combinations thereof.

6. The method of claim 2, wherein the agent is selected from: antibodies, bi-specific T-cell engagers, genetically engineered lymphocytes that express a chimeric antigen receptor (CAR), tumor infiltrating lymphocytes (TILs), and vaccines.

7. The method of claim 1, wherein the immunodeficient non-obese diabetic mouse further comprises transgenes encoding human interleukin-3 (IL-3), human granulocyte/ macrophage-stimulating factor (GM-CSF), and human steel factor (SF).

8. The method of claim 1, wherein the immunodeficient non-obese diabetic mouse has a NOD.Cg-Prkdc$^{scid}$ Il2rg$^{tm1Wjl/SzJ}$ genetic background.

9. The method of claim 1, wherein the human PDX is from a primary cancer selected from an ovarian cancer, a lung cancer, a bladder cancer, a lymphoma, a breast cancer, a brain cancer, a pancreatic cancer, a prostate cancer, a colon cancer, a colorectal cancer, an endometrial cancer, a gastric cancer, a hepatocellular cancer, a kidney/renal cancer, a skin cancer, a soft tissue carcinoma, and a sarcoma.

10. The method of claim 1, wherein the human PDX is introduced at least 12 weeks after introducing the CD34$^+$ human HSCs.

11. The method of claim 1 further comprising sub-lethally irradiating the immunodeficient non-obese diabetic mouse before introducing the CD34$^+$ human HSCs into the immunodeficient non-obese diabetic mouse.

12. The method of claim 11, wherein the immunodeficient non-obese diabetic mouse is irradiated at a dose of about 200 to 1300 cGy.

* * * * *